(12) United States Patent
Park et al.

(10) Patent No.: US 8,460,302 B2
(45) Date of Patent: Jun. 11, 2013

(54) ARTHROPLASTY DEVICES AND RELATED METHODS

(75) Inventors: Ilwhan Park, Walnut Creek, CA (US); Charlie W. Chi, Milpitas, CA (US)

(73) Assignee: OtisMed Corporation, Alameda, CA (US)

( * ) Notice: Subject to any disclaimer, the term of this patent is extended or adjusted under 35 U.S.C. 154(b) by 1171 days.

(21) Appl. No.: 11/641,382

(22) Filed: Dec. 18, 2006

(65) Prior Publication Data
US 2008/0147072 A1 Jun. 19, 2008

(51) Int. Cl.
*A61F 5/00* (2006.01)
(52) U.S. Cl.
USPC ............................................................ 606/87
(58) Field of Classification Search
USPC ............ 606/86 R–89; 700/98; 409/2, 3, 6, 409/7, 79, 80, 175, 219, 224, 227, 289, 291, 409/292
See application file for complete search history.

(56) References Cited

U.S. PATENT DOCUMENTS

| | | | |
|---|---|---|---|
| 3,195,411 | A | 7/1965 | MacDonald et al. |
| 3,825,151 | A | 7/1974 | Arnaud |
| D245,920 | S | 9/1977 | Shen |
| 4,198,712 | A | 4/1980 | Swanson |
| 4,298,992 | A | 11/1981 | Burstein |
| 4,436,684 | A | 3/1984 | White |
| D274,093 | S | 5/1984 | Kenna |
| D274,161 | S | 6/1984 | Kenna |
| 4,467,801 | A | 8/1984 | Whiteside |
| 4,575,330 | A * | 3/1986 | Hull ............................ 425/174.4 |
| 4,646,726 | A | 3/1987 | Westin et al. |
| 4,719,585 | A | 1/1988 | Cline et al. |
| 4,721,104 | A | 1/1988 | Kaufman et al. |
| 4,821,213 | A | 4/1989 | Cline et al. |
| 4,822,365 | A | 4/1989 | Walker et al. |
| 4,825,857 | A | 5/1989 | Kenna |
| 4,841,975 | A | 6/1989 | Woolson |
| 4,931,056 | A | 6/1990 | Ghajar et al. |

(Continued)

FOREIGN PATENT DOCUMENTS

| | | |
|---|---|---|
| DE | 3305237 | 2/1983 |
| DE | 4341367 C1 | 6/1995 |

(Continued)

OTHER PUBLICATIONS

Invitation to Pay Additional Fees mailed on Jul. 31, 2007, for PCT Application No. PCT/US2007/001624 filed on Jan. 19, 2007, five pages.

(Continued)

*Primary Examiner* — Kevin T Truong
*Assistant Examiner* — Christopher Beccia
(74) *Attorney, Agent, or Firm* — Polsinelli PC

(57) ABSTRACT

Methods and apparatuses for forming customized arthroplasty jigs are disclosed. Some of the apparatuses may comprise a plurality of rapid production machines and an automated mechanical system. The automated mechanical system may be configured to transport a first arthroplasty jig blank to a first rapid production machine and a second arthroplasty jig blank to a second rapid production machine. The first rapid production machine may be configured to form a first arthroplasty jig from the first arthroplasty jig blank, and the second rapid production machine may be configured to form a second arthroplasty jig from the second arthroplasty jig blank, the second arthroplasty jig having a different configuration from the first arthroplasty jig.

22 Claims, 9 Drawing Sheets

U.S. PATENT DOCUMENTS

| | | | |
|---|---|---|---|
| 4,936,862 A | 6/1990 | Walker et al. | |
| 4,976,737 A | 12/1990 | Leake | |
| 5,007,936 A | 4/1991 | Woolson | |
| 5,011,405 A | 4/1991 | Lemchen | |
| 5,027,281 A | 6/1991 | Rekow et al. | |
| 5,030,219 A | 7/1991 | Matsen, III et al. | |
| 5,037,424 A | 8/1991 | Aboczsky | |
| 5,075,866 A | 12/1991 | Goto et al. | |
| 5,078,719 A | 1/1992 | Schreiber | |
| 5,086,401 A | 2/1992 | Glassman et al. | |
| 5,098,383 A | 3/1992 | Hemmy et al. | |
| 5,099,846 A | 3/1992 | Hardy | |
| 5,122,144 A | 6/1992 | Bert et al. | |
| 5,123,927 A | 6/1992 | Duncan et al. | |
| 5,139,419 A | 8/1992 | Andreiko et al. | |
| 5,140,646 A | 8/1992 | Ueda | |
| 5,141,512 A | 8/1992 | Farmer et al. | |
| 5,154,717 A | 10/1992 | Matsen, III et al. | |
| 5,156,777 A | 10/1992 | Kaye | |
| 5,171,276 A | 12/1992 | Caspari et al. | |
| D336,518 S | 6/1993 | Taylor | |
| 5,218,427 A | 6/1993 | Koch | |
| 5,234,433 A | 8/1993 | Bert et al. | |
| 5,236,461 A | 8/1993 | Forte | |
| 5,274,565 A | 12/1993 | Reuben | |
| 5,298,115 A | 3/1994 | Leonard | |
| 5,305,203 A | 4/1994 | Raab | |
| D346,979 S | 5/1994 | Stalcup et al. | |
| 5,320,529 A | 6/1994 | Pompa | |
| 5,360,446 A * | 11/1994 | Kennedy | 128/898 |
| 5,364,402 A | 11/1994 | Mumme et al. | |
| 5,365,996 A | 11/1994 | Crook | |
| 5,368,478 A | 11/1994 | Andreiko et al. | |
| D355,254 S | 2/1995 | Krafft et al. | |
| D357,315 S | 4/1995 | Dietz | |
| 5,408,409 A | 4/1995 | Glassman et al. | |
| 5,431,562 A | 7/1995 | Andreiko et al. | |
| 5,448,489 A * | 9/1995 | Reuben | 700/163 |
| 5,452,407 A | 9/1995 | Crook | |
| 5,484,446 A | 1/1996 | Burke et al. | |
| D372,309 S | 7/1996 | Heldreth | |
| D374,078 S | 9/1996 | Johnson et al. | |
| 5,556,278 A | 9/1996 | Meitner | |
| 5,569,260 A | 10/1996 | Petersen | |
| 5,569,261 A | 10/1996 | Marik et al. | |
| 5,601,563 A | 2/1997 | Burke et al. | |
| 5,601,565 A | 2/1997 | Huebner | |
| 5,662,656 A | 9/1997 | White | |
| 5,681,354 A | 10/1997 | Eckhoff | |
| 5,682,886 A | 11/1997 | Delp et al. | |
| 5,683,398 A | 11/1997 | Carls et al. | |
| 5,690,635 A | 11/1997 | Matsen, III et al. | |
| 5,716,361 A | 2/1998 | Masini | |
| 5,725,376 A | 3/1998 | Poirier | |
| 5,735,277 A | 4/1998 | Schuster | |
| 5,741,215 A | 4/1998 | D'Urso | |
| 5,749,876 A | 5/1998 | Duvillier et al. | |
| 5,768,134 A | 6/1998 | Swaelens et al. | |
| 5,769,092 A | 6/1998 | Williamson, Jr. | |
| 5,769,859 A | 6/1998 | Dorsey | |
| D398,058 S | 9/1998 | Collier | |
| 5,810,830 A | 9/1998 | Noble et al. | |
| 5,824,085 A | 10/1998 | Sahay et al. | |
| 5,824,098 A | 10/1998 | Stein | |
| 5,824,100 A | 10/1998 | Kester et al. | |
| 5,824,111 A * | 10/1998 | Schall et al. | 623/33 |
| 5,860,980 A | 1/1999 | Axelson, Jr. et al. | |
| 5,860,981 A | 1/1999 | Bertin et al. | |
| 5,871,018 A | 2/1999 | Delp et al. | |
| 5,908,424 A | 6/1999 | Bertin et al. | |
| 5,911,724 A | 6/1999 | Wehrli | |
| 5,964,808 A | 10/1999 | Blaha et al. | |
| 5,967,777 A | 10/1999 | Klein et al. | |
| 5,993,448 A | 11/1999 | Remmler | |
| 5,995,738 A | 11/1999 | DiGioia, III et al. | |
| 6,068,658 A | 5/2000 | Insall et al. | |
| 6,090,114 A | 7/2000 | Matsuno et al. | |
| 6,096,043 A | 8/2000 | Techiera et al. | |
| 6,112,109 A * | 8/2000 | D'Urso | 600/407 |
| 6,126,690 A | 10/2000 | Ateshian et al. | |
| 6,132,447 A | 10/2000 | Dorsey | |
| 6,161,080 A | 12/2000 | Aouni-Ateshian et al. | |
| 6,171,340 B1 | 1/2001 | McDowell | |
| 6,173,200 B1 | 1/2001 | Cooke et al. | |
| 6,183,515 B1 | 2/2001 | Barlow et al. | |
| 6,228,121 B1 | 5/2001 | Khalili | |
| 6,254,639 B1 | 7/2001 | Peckitt | |
| 6,285,902 B1 | 9/2001 | Kienzle, III et al. | |
| 6,327,491 B1 | 12/2001 | Franklin et al. | |
| 6,382,975 B1 | 5/2002 | Poirier | |
| 6,385,475 B1 | 5/2002 | Cinquin et al. | |
| 6,415,171 B1 | 7/2002 | Gueziec et al. | |
| 6,458,135 B1 | 10/2002 | Harwin et al. | |
| 6,463,351 B1 * | 10/2002 | Clynch | 700/163 |
| 6,503,254 B2 | 1/2003 | Masini | |
| 6,510,334 B1 | 1/2003 | Schuster et al. | |
| 6,514,259 B2 | 2/2003 | Picard et al. | |
| 6,533,737 B1 | 3/2003 | Brosseau et al. | |
| D473,307 S | 4/2003 | Cooke | |
| 6,540,784 B2 | 4/2003 | Barlow et al. | |
| 6,558,426 B1 | 5/2003 | Masini | |
| 6,575,980 B1 | 6/2003 | Robie | |
| 6,602,259 B1 | 8/2003 | Masini | |
| 6,672,870 B2 | 1/2004 | Knapp | |
| 6,692,448 B2 | 2/2004 | Tanaka et al. | |
| 6,702,821 B2 | 3/2004 | Bonutti | |
| 6,711,431 B2 | 3/2004 | Sarin et al. | |
| 6,711,432 B2 | 3/2004 | Krause et al. | |
| 6,738,657 B1 | 5/2004 | Franklin et al. | |
| 6,747,646 B2 | 6/2004 | Gueziec et al. | |
| 6,770,099 B2 | 8/2004 | Andriacchi et al. | |
| 6,772,026 B2 * | 8/2004 | Bradbury et al. | 700/98 |
| 6,814,575 B2 | 11/2004 | Poirier | |
| 6,905,510 B2 | 6/2005 | Saab | |
| 6,923,817 B2 | 8/2005 | Carson et al. | |
| 6,932,842 B1 * | 8/2005 | Litschko et al. | 623/16.11 |
| 6,944,518 B2 * | 9/2005 | Roose | 700/117 |
| 6,969,393 B2 | 11/2005 | Pinczewski et al. | |
| 6,975,894 B2 | 12/2005 | Wehrli et al. | |
| 6,978,188 B1 | 12/2005 | Christensen | |
| 7,029,479 B2 | 4/2006 | Tallarida et al. | |
| 7,033,360 B2 | 4/2006 | Cinquin et al. | |
| 7,039,225 B2 | 5/2006 | Tanaka et al. | |
| 7,060,074 B2 | 6/2006 | Rosa et al. | |
| 7,074,241 B2 | 7/2006 | McKinnon | |
| 7,090,677 B2 | 8/2006 | Fallin et al. | |
| 7,094,241 B2 | 8/2006 | Hodorek et al. | |
| 7,104,997 B2 | 9/2006 | Lionberger et al. | |
| 7,128,745 B2 | 10/2006 | Masini et al. | |
| D532,515 S | 11/2006 | Buttler et al. | |
| 7,141,053 B2 | 11/2006 | Rose et al. | |
| 7,166,833 B2 | 1/2007 | Smith | |
| 7,172,597 B2 | 2/2007 | Sanford | |
| 7,174,282 B2 | 2/2007 | Hollister et al. | |
| 7,177,386 B2 | 2/2007 | Mostafavi et al. | |
| 7,184,814 B2 | 2/2007 | Lang et al. | |
| 7,235,080 B2 | 6/2007 | Hodorek | |
| 7,238,190 B2 | 7/2007 | Schon et al. | |
| 7,239,908 B1 | 7/2007 | Alexander et al. | |
| 7,258,701 B2 | 8/2007 | Aram et al. | |
| 7,275,218 B2 | 9/2007 | Petrella et al. | |
| 7,309,339 B2 | 12/2007 | Cusick et al. | |
| 7,340,316 B2 * | 3/2008 | Spaeth et al. | 700/98 |
| 7,359,746 B2 | 4/2008 | Arata | |
| 7,383,164 B2 | 6/2008 | Aram et al. | |
| 7,388,972 B2 | 6/2008 | Kitson | |
| 7,393,012 B2 | 7/2008 | Funakura et al. | |
| 7,394,946 B2 | 7/2008 | Dewaele | |
| 7,429,346 B2 | 9/2008 | Ensign et al. | |
| 7,468,075 B2 | 12/2008 | Lang et al. | |
| 7,517,365 B2 * | 4/2009 | Carignan et al. | 623/20.35 |
| 7,534,263 B2 * | 5/2009 | Burdulis et al. | 623/14.12 |
| 7,547,307 B2 | 6/2009 | Carson et al. | |
| 7,611,519 B2 | 11/2009 | Lefevre et al. | |
| 7,616,800 B2 | 11/2009 | Paik et al. | |
| 7,618,421 B2 | 11/2009 | Axelson, Jr. et al. | |
| 7,618,451 B2 | 11/2009 | Berez et al. | |

| | | | | | | |
|---|---|---|---|---|---|---|
| 7,630,750 B2 | 12/2009 | Liang et al. | | 2006/0030853 A1 | 2/2006 | Haines |
| 7,634,119 B2 | 12/2009 | Tsougarakis et al. | | 2006/0036257 A1 | 2/2006 | Steffensmeier |
| 7,634,306 B2 | 12/2009 | Sarin et al. | | 2006/0110017 A1 | 5/2006 | Tsai et al. |
| 7,641,660 B2 | 1/2010 | Lakin et al. | | 2006/0111628 A1 | 5/2006 | Tsai et al. |
| 7,643,862 B2 | 1/2010 | Schoenefeld | | 2006/0122491 A1 | 6/2006 | Murray et al. |
| 7,660,623 B2 | 2/2010 | Hunter et al. | | 2006/0195113 A1 | 8/2006 | Masini |
| 7,693,321 B2 | 4/2010 | Lehtonen-Krause | | 2006/0271058 A1 | 11/2006 | Ashton et al. |
| 7,702,380 B1 | 4/2010 | Dean | | 2007/0038059 A1 | 2/2007 | Sheffer et al. |
| 7,717,956 B2 | 5/2010 | Lang | | 2007/0055268 A1 | 3/2007 | Utz et al. |
| D618,796 S | 6/2010 | Cantu et al. | | 2007/0073305 A1 | 3/2007 | Lionberger et al. |
| 7,747,305 B2 | 6/2010 | Dean et al. | | 2007/0083266 A1 | 4/2007 | Lang |
| D619,718 S | 7/2010 | Gannoe et al. | | 2007/0100462 A1 | 5/2007 | Lang et al. |
| D622,854 S | 8/2010 | Otto et al. | | 2007/0106389 A1 | 5/2007 | Croxton et al. |
| 7,787,932 B2 | 8/2010 | Vilsmeier et al. | | 2007/0114370 A1 | 5/2007 | Smith et al. |
| 7,794,467 B2 | 9/2010 | McGinley et al. | | 2007/0118055 A1 | 5/2007 | McCombs |
| D626,234 S | 10/2010 | Otto et al. | | 2007/0118243 A1 | 5/2007 | Schroeder et al. |
| 7,806,896 B1 | 10/2010 | Bonutti | | 2007/0123912 A1 | 5/2007 | Carson |
| 7,842,039 B2 | 11/2010 | Hodorek et al. | | 2007/0162039 A1 | 7/2007 | Wozencroft |
| 7,842,092 B2 | 11/2010 | Otto et al. | | 2007/0167833 A1 | 7/2007 | Redel et al. |
| 7,881,768 B2 | 2/2011 | Lang et al. | | 2007/0173858 A1 | 7/2007 | Engh et al. |
| 7,894,650 B2 | 2/2011 | Weng et al. | | 2007/0191741 A1 | 8/2007 | Tsai et al. |
| 7,927,335 B2 | 4/2011 | Deffenbaugh et al. | | 2007/0198022 A1 | 8/2007 | Lang et al. |
| 7,940,974 B2 | 5/2011 | Skinner et al. | | 2007/0213738 A1 | 9/2007 | Martin et al. |
| 7,950,924 B2 | 5/2011 | Brajnovic | | 2007/0219560 A1 | 9/2007 | Hodorek |
| 7,963,968 B2 | 6/2011 | Dees, Jr. | | 2007/0226986 A1 | 10/2007 | Chi et al. |
| D642,263 S | 7/2011 | Park | | 2007/0232959 A1 | 10/2007 | Couture et al. |
| 7,974,677 B2 | 7/2011 | Mire et al. | | 2007/0233136 A1 | 10/2007 | Wozencroft |
| 8,007,448 B2 | 8/2011 | Moctezuma de La Barrera | | 2007/0233140 A1 | 10/2007 | Metzger et al. |
| 8,021,368 B2 | 9/2011 | Haines | | 2007/0233141 A1 | 10/2007 | Park et al. |
| 8,036,729 B2 | 10/2011 | Lang et al. | | 2007/0233269 A1 | 10/2007 | Steines et al. |
| 8,059,878 B2 | 11/2011 | Feilkas et al. | | 2007/0239167 A1 | 10/2007 | Pinczewski et al. |
| 8,077,950 B2 | 12/2011 | Tsougarakis et al. | | 2007/0249967 A1 | 10/2007 | Buly et al. |
| 8,086,336 B2 | 12/2011 | Christensen | | 2007/0276224 A1 | 11/2007 | Lang et al. |
| 8,126,533 B2 | 2/2012 | Lavallee | | 2007/0276400 A1 | 11/2007 | Moore et al. |
| RE43,282 E | 3/2012 | Alexander et al. | | 2007/0282451 A1 | 12/2007 | Metzger et al. |
| 8,133,234 B2 | 3/2012 | Meridew et al. | | 2007/0288030 A1 | 12/2007 | Metzger et al. |
| 8,142,189 B2 | 3/2012 | Brajnovic | | 2008/0004701 A1 | 1/2008 | Axelson et al. |
| 8,160,345 B2 | 4/2012 | Pavlovskaia et al. | | 2008/0015433 A1 | 1/2008 | Alexander et al. |
| 8,177,850 B2 | 5/2012 | Rudan et al. | | 2008/0015599 A1 | 1/2008 | D'Alessio et al. |
| 8,202,324 B2 | 6/2012 | Meulink et al. | | 2008/0015600 A1 | 1/2008 | D'Alessio et al. |
| 8,214,016 B2 | 7/2012 | Lavallee et al. | | 2008/0015602 A1 | 1/2008 | Axelson et al. |
| 8,221,430 B2 | 7/2012 | Park et al. | | 2008/0021299 A1 | 1/2008 | Meulink |
| 8,231,634 B2 | 7/2012 | Mahfouz et al. | | 2008/0031412 A1 | 2/2008 | Lang et al. |
| 8,234,097 B2 | 7/2012 | Steines et al. | | 2008/0033442 A1* | 2/2008 | Amiot et al. ............ 606/80 |
| 8,241,293 B2 | 8/2012 | Stone et al. | | 2008/0058613 A1 | 3/2008 | Lang et al. |
| 8,306,601 B2 | 11/2012 | Lang et al. | | 2008/0088761 A1 | 4/2008 | Lin et al. |
| 8,311,306 B2 | 11/2012 | Pavlovskaia et al. | | 2008/0114370 A1 | 5/2008 | Schoenefeld |
| 8,337,501 B2 | 12/2012 | Fitz et al. | | 2008/0153067 A1 | 6/2008 | Berckmans et al. |
| 2002/0087274 A1 | 7/2002 | Alexander et al. | | 2008/0161815 A1 | 7/2008 | Schoenefeld et al. |
| 2002/0160337 A1 | 10/2002 | Klein et al. | | 2008/0195108 A1 | 8/2008 | Bhatnagar et al. |
| 2003/0009167 A1 | 1/2003 | Wozencroft | | 2008/0215059 A1 | 9/2008 | Carignan et al. |
| 2003/0055502 A1 | 3/2003 | Lang et al. | | 2008/0234685 A1 | 9/2008 | Gjerde |
| 2003/0069585 A1 | 4/2003 | Axelson, Jr. et al. | | 2008/0243127 A1 | 10/2008 | Lang et al. |
| 2003/0176783 A1 | 9/2003 | Hu | | 2008/0257363 A1 | 10/2008 | Schoenefeld et al. |
| 2004/0097952 A1 | 5/2004 | Sarin et al. | | 2008/0262624 A1 | 10/2008 | White et al. |
| 2004/0098133 A1* | 5/2004 | Carignan et al. ......... 623/20.35 | | 2008/0275452 A1 | 11/2008 | Lang et al. |
| 2004/0102792 A1 | 5/2004 | Sarin et al. | | 2008/0281328 A1 | 11/2008 | Lang et al. |
| 2004/0146369 A1* | 7/2004 | Kato .......................... 409/219 | | 2008/0281329 A1 | 11/2008 | Fitz et al. |
| 2004/0147927 A1 | 7/2004 | Tsougarakis et al. | | 2008/0281426 A1 | 11/2008 | Fitz et al. |
| 2004/0153066 A1 | 8/2004 | Coon et al. | | 2008/0286722 A1 | 11/2008 | Berckmans, III et al. |
| 2004/0153079 A1 | 8/2004 | Tsougarakis et al. | | 2008/0287953 A1 | 11/2008 | Sers |
| 2004/0153087 A1 | 8/2004 | Sanford et al. | | 2008/0287954 A1 | 11/2008 | Kunz et al. |
| 2004/0243148 A1 | 12/2004 | Wasielewski | | 2008/0312659 A1 | 12/2008 | Metzger et al. |
| 2004/0243481 A1 | 12/2004 | Bradbury et al. | | 2008/0319491 A1 | 12/2008 | Schoenefeld |
| 2004/0254584 A1 | 12/2004 | Sarin et al. | | 2009/0024131 A1 | 1/2009 | Metzger et al. |
| 2005/0059978 A1 | 3/2005 | Sherry et al. | | 2009/0088763 A1 | 4/2009 | Aram et al. |
| 2005/0065617 A1 | 3/2005 | Moctezuma de la Barrera | | 2009/0089034 A1 | 4/2009 | Penney et al. |
| 2005/0096535 A1 | 5/2005 | de la Barrera | | 2009/0093816 A1 | 4/2009 | Roose et al. |
| 2005/0113841 A1 | 5/2005 | Sheldon et al. | | 2009/0110498 A1 | 4/2009 | Park |
| 2005/0148860 A1 | 7/2005 | Liew et al. | | 2009/0112213 A1 | 4/2009 | Heavener et al. |
| 2005/0192588 A1 | 9/2005 | Garcia | | 2009/0131941 A1 | 5/2009 | Park et al. |
| 2005/0216024 A1 | 9/2005 | Massoud | | 2009/0138020 A1 | 5/2009 | Park et al. |
| 2005/0234461 A1* | 10/2005 | Burdulis et al. ............ 606/79 | | 2009/0151736 A1 | 6/2009 | Belcher et al. |
| 2005/0245934 A1 | 11/2005 | Tuke et al. | | 2009/0157083 A1 | 6/2009 | Park et al. |
| 2005/0245936 A1 | 11/2005 | Tuke et al. | | 2009/0163923 A1 | 6/2009 | Flett et al. |
| 2005/0256389 A1 | 11/2005 | Koga et al. | | 2009/0222014 A1 | 9/2009 | Bojarski et al. |
| 2006/0015018 A1 | 1/2006 | Jutras et al. | | 2009/0222015 A1 | 9/2009 | Park et al. |
| 2006/0015030 A1 | 1/2006 | Poulin et al. | | 2009/0222016 A1 | 9/2009 | Park et al. |
| 2006/0015188 A1 | 1/2006 | Grimes | | 2009/0222103 A1 | 9/2009 | Fitz et al. |

| | | |
|---|---|---|
| 2009/0248044 A1 | 10/2009 | Amiot et al. |
| 2009/0254093 A1 | 10/2009 | White et al. |
| 2009/0254367 A1 | 10/2009 | Belcher et al. |
| 2009/0270868 A1 | 10/2009 | Park et al. |
| 2009/0274350 A1 | 11/2009 | Pavlovskaia et al. |
| 2009/0276045 A1 | 11/2009 | Lang |
| 2009/0306676 A1 | 12/2009 | Lang et al. |
| 2009/0307893 A1 | 12/2009 | Burdulis, Jr. et al. |
| 2009/0312805 A1 | 12/2009 | Lang et al. |
| 2010/0023015 A1 | 1/2010 | Park |
| 2010/0042105 A1 | 2/2010 | Park et al. |
| 2010/0049195 A1 | 2/2010 | Park et al. |
| 2010/0087829 A1 | 4/2010 | Metzger et al. |
| 2010/0152741 A1 | 6/2010 | Park et al. |
| 2010/0160917 A1 | 6/2010 | Fitz et al. |
| 2010/0168754 A1 | 7/2010 | Fitz et al. |
| 2010/0174376 A1 | 7/2010 | Lang |
| 2010/0191242 A1 | 7/2010 | Massoud |
| 2010/0198351 A1 | 8/2010 | Meulink |
| 2010/0228257 A1 | 9/2010 | Bonutti |
| 2010/0256479 A1 | 10/2010 | Park et al. |
| 2010/0274534 A1 | 10/2010 | Steines et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0015636 A1 | 1/2011 | Katrana et al. |
| 2011/0029093 A1 | 2/2011 | Bojarski et al. |
| 2011/0046735 A1 | 2/2011 | Metzger et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071581 A1 | 3/2011 | Lang et al. |
| 2011/0087332 A1 | 4/2011 | Bojarski et al. |
| 2011/0092804 A1 | 4/2011 | Schoenefeld et al. |
| 2011/0092978 A1 | 4/2011 | McCombs |
| 2011/0144760 A1 | 6/2011 | Wong et al. |
| 2011/0160736 A1 | 6/2011 | Meridew et al. |
| 2011/0166578 A1 | 7/2011 | Stone et al. |
| 2011/0166666 A1 | 7/2011 | Meulink et al. |
| 2011/0172672 A1 | 7/2011 | Dubeau et al. |
| 2011/0190899 A1 | 8/2011 | Pierce et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0218539 A1 | 9/2011 | Fitz et al. |
| 2011/0218584 A1 | 9/2011 | Fitz et al. |
| 2011/0230888 A1 | 9/2011 | Lang et al. |
| 2011/0238073 A1 | 9/2011 | Lang et al. |
| 2011/0268248 A1 | 11/2011 | Simon et al. |
| 2011/0270072 A9 | 11/2011 | Feilkas et al. |
| 2011/0276145 A1 | 11/2011 | Carignan et al. |
| 2011/0282473 A1 | 11/2011 | Pavlovskaia et al. |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0319897 A1 | 12/2011 | Lang et al. |
| 2011/0319900 A1 | 12/2011 | Lang et al. |
| 2012/0029520 A1 | 2/2012 | Lang et al. |
| 2012/0041446 A1 | 2/2012 | Wong et al. |
| 2012/0053591 A1 | 3/2012 | Haines et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0093377 A1 | 4/2012 | Tsougarakis et al. |
| 2012/0101503 A1 | 4/2012 | Lang et al. |
| 2012/0143197 A1 | 6/2012 | Lang et al. |
| 2012/0150243 A9 | 6/2012 | Crawford et al. |
| 2012/0151730 A1 | 6/2012 | Fitz et al. |
| 2012/0158001 A1 | 6/2012 | Burdulis, Jr. et al. |
| 2012/0158002 A1 | 6/2012 | Carignan et al. |
| 2012/0165821 A1 | 6/2012 | Carignan et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0215226 A1 | 8/2012 | Bonutti |
| 2012/0230566 A1 | 9/2012 | Dean et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski et al. |
| 2012/0265499 A1 | 10/2012 | Mahfouz et al. |
| 2012/0310400 A1 | 12/2012 | Park |

FOREIGN PATENT DOCUMENTS

| | | |
|---|---|---|
| DE | 10 2005 023 028 A1 | 11/2006 |
| EP | 0097001 A | 12/1983 |
| EP | 0574098 A | 12/1993 |
| EP | 0622052 A | 11/1994 |
| EP | 0908836 A2 | 4/1999 |
| EP | 0908836 A3 | 12/1999 |
| EP | 1059153 A2 | 12/2000 |
| EP | 1486900 | 12/2004 |
| EP | 1 532 939 A1 | 5/2005 |
| GB | 2215610 | 9/1989 |
| GB | 2420717 A | 6/2006 |
| WO | WO 95/07509 A1 | 3/1995 |
| WO | WO 95/27450 | 10/1995 |
| WO | WO 97/23172 A2 | 7/1997 |
| WO | WO 98/12995 A2 | 4/1998 |
| WO | WO-01/00096 A1 | 1/2001 |
| WO | WO 01/85040 A1 | 11/2001 |
| WO | WO 02/096268 A2 | 12/2002 |
| WO | WO 2005/087125 A2 | 9/2005 |
| WO | WO 2006/134345 A1 | 12/2006 |
| WO | WO 2007/058632 A1 | 5/2007 |
| WO | WO 2007/092841 A2 | 8/2007 |

OTHER PUBLICATIONS

Author Unknown, "MRI Protocol Reference," ConforMIS, Inc., copyright 2007, http://www.conformis.com/Imaging-Professionals/MRI-Protocol-Guides, last visited on Mar. 28, 2008, 18 pages.

Author Unknown, "MRI Protocol Reference Guide for GE Systems," ConforMIS, Inc., copyright 2007, http://www.conformis.com/Imaging-Professionals/MRI-Protocol-Guides, last visited on Mar. 28, 2008, 18 pages.

Author Unknown, "MRI Protocol Reference Guide for Phillips Systems," ConforMIS, Inc., copyright 2007, http://www.conformis.com/Imaging-Professionals/MRI-Protocol-Guides, last visited on Mar. 28, 2008, 19 pages.

Author Unknown, "MRI Protocol Reference Guide for Siemens Systems," ConforMIS, Inc., copyright 2007, http://www.conformis.com/Imaging-Professionals/MRI-Protocol-Guides, last visited on Mar. 28, 2008, 18 pages.

Barequet et al., "Filling Gaps in the Boundary of a Polyhedron," *Computer Aided Geometric Design*, vol. 12, pp. 207-229, 1995.

Barequet et al., "Repairing CAD Models," Proceedings of the 8th IEEE Visualization '97 Conference, pp. 363-370, Oct. 1997.

Biščević et al., "Variations of Femoral Condyle Shape," *Coll. Antropol.*, vol. 29 No. 2, pp. 409-414, 2005.

Bøhn et al., "A Topology-Based Approach for Shell-Closure," *Geometric Modeling for Product Realization* (P.R. Wilson et al. editors), pp. 297-319, Elsevier Science Publishers B.V., North-Holland, 1993.

Couglin et al., "Tibial Axis and Patellar Position Relative to the Femoral Epicondylar Axis During Squatting," *The Journal of Arthroplasty*, vol. 18, No. 8, Elsevier, 2003.

Eckhoff et al., "Three-Dimensional Mechanics, Kinematics, and Morphology of the Knee Viewed in Virtual Realty," *The Journal of Bone and Joint Surgery*, vol. 87-A, Supplement 2, pp. 71-80, 2005.

Erikson, "Error Correction of a Large Architectural Model: The Henderson County Courthouse," Technical Report TR95-013, Dept. of Computer Science, University of North Carolina at Chapel Hill, pp. 1-11, 1995.

Ervin et al., *Landscape Modeling*, McGraw-Hill, New York, NY, 8 pages (Table of Contents), 2001.

Farin, *NURB Curves and Surfaces: From Projective Geometry to Practical Use*, AK Peters, Wellesley, MA, 7 pages (Table of Contents), 1995.

Fleischer et al., "Accurate Polygon Scan Conversion Using Half-Open Intervals," *Graphics Gems III*, pp. 362-365, code: pp. 599-605, 1992.

Grüne et al., "On numerical algorithm and interactive visualization for optimal control problems," *Journal of Computation and Visualization in Science*, vol. 1, No. 4, pp. 221-229, Jul. 1999.

Guéziec et al., "Converting Sets of Polygons to Manifold Surfaces by Cutting and Stitching," Proc. IEEE Visualization 1998, pp. 383-390, Oct. 1998.

Jones et al., "A new approach to the construction of surfaces from contour data," *Computer Graphics Forum*, vol. 13, No. 3, pp. 75-84, 1994 [ISSN 0167-7055].

Khorramabadi, "A Walk Through the Planned CS Building," Technical Report UCB/CSD 91/652, Computer Science Department, University of California at Berkeley, 74 pages, 1991.

Kumar, *Robust Incremental Polygon Triangulation for Surface Rendering*, Center for Geometric Computing, Department of Computer Science, Johns Hopkins University, Baltimore, MD, WSCG, The International Conference in Central Europe on Computer Graphics, Visualization and Computer Vision, pp. 381-388, 2000.

Lorensen et al., "Marching Cubes: A High Resolution 3d Surface Construction Algorithm," *Computer Graphics*, vol. 21, No. 4, pp. 163-169, 1987.

Nooruddin et al., Simplification and Repair of Polygonal Models Using Volumetric Techniques, *IEEE Transactions on Visualization and Computer Graphics*, vol. 9, No. 2, pp. 191-205, Apr.-Jun. 2003.

Rohlfing et al., "Quo Vadis, Atlas-Based Segmentation?", *The Handbook of Medical Image Analysis: Segmentation and Registration Models* (Kluwer), pp. 1-55, (http://www.stanford.edu/~rohlfing/publications/2005-rohlfing-chapter-quo_vadis_atlas_based_segmentation.pdf).

Office Action, U.S. Appl. No. 10/146,862, mailed Jan. 13, 2005, 10 pages.

Amendment and Response to Office Action and Petition to Revive, U.S. Appl. No. 10/146,862, filed Jan. 18, 2006, 29 pages.

International Search Report and Written Opinion, PCT/US2007/001624, dated Dec. 12, 2007, 14 pages.

International Search Report and Written Opinion, PCT/US2007/001622, dated Jun. 11, 2007, 14 pages.

International Search Report and Written Opinion, International Patent Application No. PCT/US2008/083125, dated Mar. 9, 2009, 13 pages.

Restriction Requirement, U.S. Appl. No. 11/641,569, mailed Apr. 27, 2009, 7 pages.

International Search Report and Written Opinion, International Application No. PCT/US2009/34983, mailed May 22, 2009, 15 pages.

International Search Report and Written Opinion, International Application No. PCT/US2009/034967, mailed Jun. 16, 2009, 15 pages.

International Search Report and Written Opinion, International Application No. PCT/US2009/041519, mailed Jun. 17, 2009, 10 pages.

Kunz et al., "Computer Assisted Hip Resurfacing Using Individualized Drill Templates," The Journal of Arthroplasty, vol. 00, No. 0, pp. 1-7, 2009.

International Search Report and Written Opinion, International Application No. PCT/US2009/040629, mailed Aug. 6, 2009, 9 pages.

Restriction Requirement, U.S. Appl. No. 11/642,385, mailed Oct. 27, 2009, 7 pages.

International Search Report and Written Opinion, International Application No. PCT/US2009/051109, mailed Nov. 6, 2009, 13 pages.

NonFinal Office Action, U.S. Appl. No. 11/641,569, mailed Nov. 12, 2009, 9 pages.

Restriction Requirement, U.S. Appl. No. 11/656,323, mailed Nov. 13, 2009, 10 pages.

International Search Report and Written Opinion, International Application No. PCT/US2009/058946, mailed Jan. 28, 2010, 14 pages.

Non-Final Office Action and PTO-892, U.S. Appl. No. 11/642,385, mailed Mar. 2, 2010, 11 pages.

International Search Report and Written Opinion, International Application No. PCT/US2009/068055, mailed Mar. 11, 2010, 10 pages.

Non-Final Office Action and PTO-892, U.S. Appl. No. 11/656,323, mailed Mar. 30, 2010, 10 pages.

Stulberg et al., "Computer-and Robot-Assisted Orthopaedic Surgery", *Computer-Integrated Surgery Technology and Clinical Applications*, edited by Taylor et al., Massachusetts Institute of Technology, Chapter 27, pp. 373-378, 1996.

Kienzel III et al., "An Integrated CAD-Robotics System for Total Knee Replacement Surgery", *IEEE International Conference*, pp. 889-894, vol. 1, May 1993.

U.S. Appl. No. 10/146,862, filed May 15, 2002, Park et al., (abandoned).

U.S. Appl. No. 29/296,687, filed Oct. 25, 2007, Park.

U.S. Appl. No. 13/086,275, filed Apr. 13, 2011, Park et al.

U.S. Appl. No. 13/066,568, filed Apr. 18, 2011, Pavlovskaia et al.

Advisory Action, U.S. Appl. No. 11/642,385, dated Oct. 29, 2010, 3 pages.

European Search Report, 10192631.9-2310, dated Mar. 17, 2011, 5 pages.

Ex Parte Quayle Action, U.S. Appl. No. 29/296,687, mailed Jan. 24, 2011, 11 pages.

International Preliminary Report on Patentability, PCT/US2007/001624, dated Aug. 19, 2008, 8 pages.

International Preliminary Report on Patentability, PCT/US2007/001622, dated Dec. 28, 2009, 7 pages.

International Preliminary Report on Patentability, PCT/US2008/083125, dated Jul. 1, 2010, 10 pages.

International Preliminary Report on Patentability, PCT/US2009/034967, dated Nov. 11, 2010, 13 pages.

International Preliminary Report on Patentability, PCT/US2009/040629, dated Nov. 11, 2010, 8 pages.

International Preliminary Report on Patentability, PCT/US2009/041519, dated Nov. 11, 2010, 9 pages.

International Preliminary Report on Patentability, PCT/US2009/051109, dated Feb. 3, 2011, 12 pages.

Nonfinal Office Action, U.S. Appl. No. 11/959,344, dated Feb. 15, 2011, 29 pages.

Notice of Allowance, U.S. Appl. No. 29/296,687, mailed Mar. 31, 2011, 18 pages.

RCE/Amendment, U.S. Appl. No. 11/642,385, filed Dec. 6, 2010, 13 pages.

RCE/Amendment, U.S. Appl. No. 11/656,323, filed Nov. 19, 2010, 12 pages.

Response to Ex Parte Quayle Action, U.S. Appl. No. 29/296,687, dated Mar. 24, 2011, 17 pages.

Response to Restriction Requirement, U.S. Appl. No. 11/959,344, filed Nov. 24, 2010, 13 pages.

Restriction Requirement, U.S. Appl. No. 11/959,344, dated Oct. 29, 2010, 6 pages.

Amendment and Response to Office Action, U.S. Appl. No. 11/656,323, filed Jun. 25, 2010, 7 pages.

Amendment and Response to Office Action, U.S. Appl. No. 11/641,569, dated Feb. 5, 2010, 20 pages.

Amendment and Response to Restriction Requirement, U.S. Appl. No. 11/641,569, dated May 27, 2009, 12 pages.

Amendment and Response to Restriction Requirement, U.S. Appl. No. 11/642,385, filed Nov. 24, 2009, 10 pages.

Amendment and Response to Restriction/Election Requirement, U.S. Appl. No. 11/656,323, filed Dec. 8, 2009, 6 pages.

Amendment and Response, U.S. Appl. No. 11/642,385, filed May 28, 2010, 11 pages.

Amendment and Response to Final Office Action, U.S. Appl. No. 11/642,385, filed Oct. 4, 2010, 16 pages.
Final Office Action and PTO-892, U.S. Appl. No. 11/642,385, mailed Aug. 5, 2010, 10 pages.
Final Office Action and PTO-892, U.S. Appl. No. 11/656,323, mailed Sep. 3, 2010, 11 pages.
Final Office Action, U.S. Appl. No. 11/641,569, mailed May 10, 2010, 9 pages.
International Preliminary Report on Patentability, PCT/US2009/034983, dated Sep. 10, 2010, 13 pages.
Notice of Non-Compliant Amendment, U.S. Appl. No. 11/641,569, mailed Aug. 7, 2009, 3 pages.
Preliminary Amendment, U.S. Appl. No. 11/641,569, dated Aug. 14, 2008, 13 pages.
Preliminary Amendment, U.S. Appl. No. 11/642,385, filed Aug. 22, 2008, 42 pages.
RCE/Amendment, U.S. Appl. No. 11/641,569, filed Aug. 9, 2010.
Response to Notice of Non-Complaint Amendment, U.S. Appl. No. 11/641,569, dated Aug. 19, 2009, 11 pages.
Response to Restriction Requirement U.S. Appl. No. 29/296,687, filed Oct. 7, 2010, 3 pages.
Restriction Requirement, U.S. Appl. No. 29/296,687, mailed Sep. 21, 2010, 7 pages.
Akca, "Matching of 3D Surfaces and Their Intensities," ISPRS Journal of Photogrammetry & Remote Sensing, 62(2007), 112-121.
Arima et al., "Femoral Rotational Alignment, Based on the Anteroposterior Axis, in Total Knee Arthroplasty in a Valgus Knee. A Technical Note," Journal Bone Joint Surg Am. 1995;77(9):1331-4.
Bargar et al., "Robotic Systems in Surgery," Orthopedic and Spine Surgery, Surgical Technology International II, 1993, 419-423.
Besl et al., "A Method for Registration of 3-D Shapes," IEEE Transactions on Pattern Analysis and Machine Intelligence (PAMI), 14(2):239-256, Feb. 1992.
Blaha et al., "Using the Transepicondylar Axis to Define the Sagittal Morphology of the Distal Part of the Femur," J Bone Joint Surg Am. 2002;84-A Suppl 2:48-55.
Bullough et al., "The Geometry of Diarthrodial Joints, Its Physiologic Maintenance and the Possible significance of Age-Related Changes in Geometry-to-Load distribution and the Development of Osteoarthritis," Clin Orthop Rel Res 1981, 156:61-6.
Burgkart et al., "Magnetic Resonance Imaging-Based Assessment of Cartilage Loss in Severe Osteoarthritis: Accuracy, Precision, and Diagnostic Value," Arthritis Rheum 2001, 44:2072-7.
Canny, "A computational Approach to Edge Detection," IEEE Transactions on Pattern Analysis and Machine Intelligence, PAMI 8(6), pp. 679-698 (1986).
Churchill et al., "The Transepicondylar Axis Approximates the Optimal Flexion Axis of the Knee," Clin Orthop Relat Res. 1998(356):111-8.
Cicuttini et al., "Gender Differences in Knee Cartilage Volume as Measured by Magnetic Resonance Imaging," Osteoarthritis Cartilage 1999, 7:265-71.
Cicuttini et al., "Longitudinal Study of the Relationship Between Knee angle and Tibiofemoral cartilage Volume in Subjects with Knee Osteoarthritis," Rheumatology (Oxford) 2004, 43:321-4.
Eckhoff et al., "Difference Between the Epicondylar and Cylindrical Axis of the Knee," Clin Orthop Relat Res. 2007;461:238-44.
Eisenhart-Rothe et al., "Femorotibial and Patellar Cartilage Loss in Patients Prior to Total Knee arthroplasty, Heterogeneity, and Correlation with alignment of the Knee," Ann Rheum Dis., Jun. 2005 (BMJ Publishing Group Ltd & European League Against Rheumatism).
Eisenhart-Rothe et al., "The Role of Knee alignment in Disease Progression and Functional Decline in Knee Osteoarthritis," JAMA 2001, 286:188-95.
Elias et al., "A Correlative Study of the Geometry and anatomy of the Distal Femur," Clinical Orthopaedics and Related Research 1990(260):98-103.
Favorito et al., "total Knee Arthroplasty in the Valgus Knee," Journal Am Acad Orthop surg. 2002;10(1):16-24.
Freeman et al., "The Movement of the Knee Studied by Magnetic Resonance Imaging," Clinical Orthopaedics and Related Research 2003(410):35-43.

Freeman et al., "The Movement of the Normal Tibio-Femoral Joint," Journal Biomech. 2005;38(2):197-208.
Graichen et al., "Quantitative Assessment of Cartilage Status in Osteoarthritis by Quantitative Magnetic Resonance Imaging: Technical Validation for Use in analysis of Cartilage Volume and Further Morphologic Parameters," Arthritis Rheum 2004, 50:811-16.
Gruen et al., "Least Squares 3D Surface and Curve Matching," ISPRS Journal of Photogrammetry & Remote Sensing, 59(2005), 151-174.
Hollister et al., "The Axes of Rotation of the Knee," Clinical Orthopaedics and Related Research 1993(290):259-68.
Howell et al., "Longitudinal Shapes of the Tibia and Femur are Unrelated and Variable," Clinical Orthopaedics and Related Research (2010) 468: 1142-1148.
Howell et al., "Results of an Initial Experience with Custom-Fit Positioning Total Knee Arthroplasty in a Series of 48 Patients," Orthopedics, 2008;31(9):857-63.
Howell et al., "In Vivo Adduction and Reverse Axial Rotation (External) of the Tibial Component can be Minimized During Standing and Kneeling," Orthopedics, In Press.
Iwaki et al., "Tibiofemoral Movement 1: The Shapes and Relative Movements of the Femur and Tibia in the Unloaded Cadaver Knee," Journal Bone Joint Surg Br. 2000;82(8):1189-95.
Jacobs et al., "Hip Resurfacing Through an Anterolateral Approach," J. Bone Joint Surg Am. 2008:90 Suppl 3:38-44.
Johnson, "Joint Remodeling as the Basis for Osteoarthritis," Journal Am Vet Med Assoc. 1962, 141:1233-41.
Kass et al., "Active Contour Models," International Journal of Computer Vision, pp. 321-331 (1988).
Kellgren et al., "Radiological Assessment of Osteoarthrosis," Ann Rheum Dis 1957, 10:494-501.
Kessler et al, "Sagittal Curvature of Total Knee Replacements Predicts in vivo Kinematics," Clin Biomech (Bristol, Avon) 2007; 22(1):52-8.
Kienzel III et al., "Total Knee Replacement," IEEE May/Jun. 1995.
Krackow et al., "Flexion-Extension Joint Gap Changes After Lateral Structure Release for Valgus Deformity Correction in Total Knee Arthroplasty: A Cadaveric Study," Journal Arthroplasty, 1999;14(8):994-1004.
Krackow et al., "Primary Total Knee Arthroplasty in Patients with Fixed Valgus Deformity," Clin Orthop Relat Res. 1991(273):9-18.
Krackow, "Approaches to Planning lower Extremity alignment for Total Knee arthroplasty and Osteotomy About the Knee," adv Orthop surg 7:69, 1983.
Lea et al., "Registration and immobilization in robot-assisted surgery", Journal of Image Guided Surgery, pp. 1-10, 1995.
Manner et al., "Knee Deformity in Congenital Longitudinal Deficiencies of the Lower Extremity," Clin Orthop Relat Res. 2006;448:185-92.
Matsuda et al., "Anatomical Analysis of the Femoral Condyle in Normal and Osteoarthritic Knees," Journal Orthopaedic Res. 2004;22(1):104-9.
Matsuda et al., "Femoral Condyle Geometry in the Normal and Varus Knee," Clinical Orthop Relat Res. 1998(349):183-8.
Messmer et al., "Volumetric Model Determination of the Tibia Based on 2d Radiographs Using a 2d/3d Database", Dept. of Surgery, Trauma Unit, University Hospital, Basel, Switzerland, *Computer Aided Surgery* 6:183-194 (2001).
Mihalko et al., The Variability of Intramedullary Alignment of the Femoral Component During Total Knee Arthroplasty, Journal Arthroplasty. 2005;20(1):25-8.
Morvan et al., IVECS, Interactively Correcting .STL Files in a Virtual Environment, Clemson University, Clemson, SC, Proc. Conf. Virtual Design, Aug. 1996.
Naoki Kusumoto, Taiji et al., "Application of Virtual Reality Force Feedback Haptic Device for Oral Implant Surgery", Graduate School of Dentistry Course for Integrated Oral Science and Stomatology, Jun. 16, 2005.
Panjabi et al., "Errors in Kinematic Parameters of a Planar Joint: Guidelines for Optimal Experimental Design," Journal Biomech. 1982;15(7):537-44.

Perillo-Marcone et al., "Effect of Varus/Valgus Malalignment on Bone Strains in the Proximal Tibia After TKR: An Explicit Finite element Study," Journal Biomechanical Engineering 2007, vol. 129, 1:1-11.

Peterfy et al., "Quantification of articular Cartilage in the Knee with Pulsed Saturation Transfer Subtraction and Fact-Suppressed MR Imaging: Optimization and Validation," Radiology 1994, 192:485-91.

Pinskerova et al., "The Shapes and Relative Movements of the Femur and Tibia at the Knee," Orthopaedics 2000;29 Suppl 1:S3-5.

Rosset et al., "General Consumer Communication Tools for Improved Image Management and Communication in Medicine," Journal Digital Imaging, 2005;18(4):270-9.

Shakespeare D., "Conventional Instruments in Total Knee Replacement: What Should We Do With Them?" Knee. 2006;13(1):1-6.

Shepstone et al., "The shape of the Distal Femur: A Palaeopathological Comparison of Eburnated and Non-Eburnated Femora," Ann. Rheum Dis. 1999, 58:72-8.

Siston et al., "The Variability of Femoral Rotational Alignment in Total Knee Arthroplasty," Journal Bone Joint Surg Am. 2005;87(10):2276-80.

Siston et al., "Averaging Different Alignment Axes Improves Femoral Rotational Alignment in Computer-Navigated Total Knee Arthroplasty," Journal Bone Joint Surg Am. 2008;90(10):2098-104.

Soudan et al., "Methods, Difficulties and Inaccuracies in the Study of Human Joint Kinematics and Pathokinematics by the Instant axis Concept. Example: The Knee Joint," Journal Biomech. 1979;12(1):27-33.

Spencer et al., "Initial Experience with Custom-Fit Total Knee Replacement: Intra-operative Events and Long-Leg Coronal alignment," International Orthopaedics (SICOT), 2009:In Press.

Teeny et al., "Primary Total Knee Arthroplasty in Patients with Severe Varus Deformity. A Comparative Study," Clin Orthop Relat Res. 1991(273):19-31.

Wright Medical Technology, Inc., "Prophecy Pre-Operative Naviation Guides Surgical Technique," 2009.

Amendment and Response to Non-Final Office Action, U.S. Appl. No. 11/959,344, dated Jul. 15, 2011, 13 pages.

International Search Report and Written Opinion, PCT/US2011/032342, dated Jul. 1, 2011, 8 pages.

Non-Final Office Action, U.S. Appl. No. 11/641,569, dated Aug. 3, 2011, 14 pages.

Non-Final Office Action, U.S. Appl. No. 12/390,667, dated Aug. 24, 2011, 49 pages.

Response to Restriction Requirement, U.S. Appl. No. 12/390,667, dated Jul. 27, 2011, 8 pages.

Response to Restriction Requirement, U.S. Appl. No. 12/391,008, filed Aug. 29, 2011, 9 pages.

Restriction Requirement, U.S. Appl. No. 11/946,002, dated Sep. 1, 2011, 8 pages.

Restriction Requirement, U.S. Appl. No. 12/390,667, dated Jul. 14, 2011, 9 pages.

Restriction Requirement, U.S. Appl. No. 12/391,008, dated Aug. 18, 2011, 6 pages.

U.S. Appl. No. 29/394,882, filed Jun. 22, 2011, Ilwhan Park.

U.S. Appl. No. 13/374,960, filed Jan. 25, 2012, Pavlovskaia et al.

U.S. Appl. No. 13/488,505, filed Jun. 5, 2012, Ilwhan Park et al.

Advisory Action and Interview Summary, U.S. Appl. No. 12/390,667, mailed Apr. 27, 2012, 23 pages.

Final Office Action, U.S. Appl. No. 11/959,344, mailed Oct. 27, 2011, 12 pages.

Final Office Action, U.S. Appl. No. 12/390,667, mailed Jan. 13, 2012, 27 pages.

Final Office Action, U.S. Appl. No. 11/641,569, mailed Mar. 1, 2012, 12 pages.

Final Office Action, U.S. Appl. No. 11/946,002, mailed May 9, 2012, 24 pages.

Final Office Action, U.S. Appl. No. 12/391,008, mailed May 17, 2012, 28 pages.

Non-Final Office Action, U.S. Appl. No. 11/924,425, mailed Jan. 25, 2012, 35 pages.

Non-Final Office Action, U.S. Appl. No. 11/946,002, dated Nov. 25, 2011, 44 pages.

Non-Final Office Action, U.S. Appl. No. 12/386,105, dated Feb. 9, 2012, 30 pages.

Non-Final Office Action, U.S. Appl. No. 12/391,008, mailed Oct. 31, 2011, 44 pages.

Notice of Allowance, U.S. Appl. No. 13/066,568, mailed Oct. 26, 2011, 28 pages.

Notice of Allowance, U.S. Appl. No. 11/959,344, mailed Mar. 5, 2012, 13 pages.

Response to Final Office Action, U.S. Appl. No. 11/959,344, filed Dec. 27, 2011, 16 pages.

Response to Final Office Action, U.S. Appl. No. 12/390,667, filed Mar. 12, 2012, 19 pages.

Response to Non-Final Office Action, U.S. Appl. No. 12/390,667, filed Nov. 18, 2011, 16 pages.

Response to Non-Final Office Action, U.S. Appl. No. 11/641,569, filed Dec. 2, 2011, 7 pages.

Response to Non-Final Office Action, U.S. Appl. No. 11/924,425, filed Apr. 25, 2012, 8 pages.

Response to Non-Final Office Action, U.S. Appl. No. 12/386,105, filed Jun. 8, 2012, 13 pages.

Response to Non-Final Office Action, U.S. Appl. No. 12/391,008, filed Feb. 24, 2012, 18 pages.

Response to Non-Final Office Action, U.S. Appl. No. 11/946,002, filed Mar. 8, 2012, 16 pages.

Response to Restriction Requirement, U.S. Appl. No. 12/386,105, filed Dec. 21, 2011, 9 pages.

Response to Restriction Requirement, U.S. Appl. No. 12/111,924, filed Apr. 16, 2012, 8 pages.

Response to Restriction Requirement, U.S. Appl. No. 12/636,939, filed Apr. 19, 2012, 6 pages.

Response to Restriction Requirement, U.S. Appl. No. 12/563,809, filed Feb. 24, 2012, 10 pages.

Response to Restriction, U.S. Appl. No. 11/924,425, filed Nov. 8, 2011, 5 pages.

Response to Restriction, U.S. Appl. No. 11/946,002, filed Sep. 23, 2011, 7 pages.

Response to Restriction, U.S. Appl. No. 12/505,056, filed Apr. 11, 2012, 9 pages.

Response to Restriction, U.S. Appl. No. 12/546,545, filed Jun. 4, 2012, 7 pages.

Restriction Requirement, U.S. Appl. No. 11/924,425, dated Oct. 13, 2011, 6 pages.

Restriction Requirement, U.S. Appl. No. 12/111,924, mailed Mar. 19, 2012, 8 pages.

Restriction Requirement, U.S. Appl. No. 12/386,105, dated Oct. 24, 2011, 7 pages.

Restriction Requirement, U.S. Appl. No. 12/505,056, mailed Mar. 14, 2012, 8 pages.

Restriction Requirement, U.S. Appl. No. 12/546,545, mailed May 3, 2012, 8 pages.

Restriction Requirement, U.S. Appl. No. 12/636,939, mailed Apr. 13, 2012, 6 pages.

Restriction Requirement, U.S. Appl. No. 12/563,809, dated Feb. 2, 2012, 7 pages.

Appeal Brief, U.S. Appl. No. 12/390,667, filed Jul. 12, 2012, 32 pages.

Final Office Action, U.S. Appl. No. 11/924,425, mailed Jul. 6, 2012, 14 pages.

Non-Final Office Action, U.S. Appl. No. 12/111,924, mailed Jun. 29, 2012, 35 pages.

Non-Final Office Action, U.S. Appl. No. 12/546,545, mailed Jul. 19, 2012, 28 pages.

Non-Final Office Action, U.S. Appl. No. 12/563,809, mailed Sep. 21, 2012, 32 pages.

Non-Final Office Action, U.S. Appl. No. 12/636,939, mailed Jul. 20, 2012, 25 pages.

Non-Final Office Action, U.S. Appl. No. 13/374,960, mailed Aug. 1, 2012, 6 pages.

Notice of Allowance, U.S. Appl. No. 12/386,105, mailed Jul. 5, 2012, 11 pages.

RCE/Amendment, U.S. Appl. No. 11/946,002, filed Sep. 6, 2012, 38 pages.

Response to Final Office Action, U.S. Appl. No. 11/641,569, filed Jun. 28, 2012, 10 pages.
Response to Final Office Action, U.S. Appl. No. 11/924,425, filed Sep. 5, 2012, 9 pages.
Response to Restriction, U.S. Appl. No. 12/563,809, filed Aug. 6, 2012, 10 pages.
Restriction Requirement, U.S. Appl. No. 12/563,809, mailed Jul. 6, 2012, 6 pages.
Amendment Under 37 C.F.R. 1.312, U.S. Appl. No. 12/386,105, filed Oct. 1, 2012, 6 pages.
Appeal Brief, U.S. Appl. No. 12/391,008, filed Oct. 16, 2012, 24 pages.
Examiner's Answer in appeal, U.S. Appl. No. 12/391,008, mailed Dec. 13, 2012, 27 pages.
Howell et al., "In Vivo Adduction and Reverse Axial Rotation (External) of the Tibial Component can be Minimized During Standing and Kneeling," Orthopedics|ORTHOSupersite.com vol. 32 No. 5, 319-326 (May 2009).
Non-Final Office Action, U.S. Appl. No. 12/390,667, mailed Sep. 26, 2012, 21 pages.
Notice of Allowance, U.S. Appl. No. 11/924,425, mailed Sep. 25, 2012, 18 pages.
Notice of Allowance, U.S. Appl. No. 13/374,960, mailed Nov. 2, 2012, 24 pages.
Response to Non-Final Office Action, U.S. Appl. No. 12/563,809, filed Dec. 13, 2012, 15 pages.
Response to Non-Final Office Action, U.S. Appl. No. 12/111,924, filed Sep. 28, 2012, 10 pages.
Response to Non-Final Office Action, U.S. Appl. No. 12/636,939, filed Oct. 10, 2012, 8 pages.
Response to Non-Final Office Action, U.S. Appl. No. 12/546,545, filed Oct. 19, 2012, 15 pages.
U.S. Appl. No. 13/573,662, filed Oct. 2, 2012, Pavlovskaia et al.
Final Office Action, U.S. Appl. No. 12/546,545, dated Dec. 20, 2012, 16 pages.
Non-Final Office Action, U.S. Appl. No. 11/641,569, dated Jan. 3, 2013, 12 pages.
Notice of Allowance, U.S. Appl. No. 12/111,924, dated Dec. 24, 2012, 10 pages.
Restriction Requirement, U.S. Appl. No. 13/573,662, mailed Jan. 17, 2013, 6 pages.
U.S. Appl. No. 13/723,904, filed Dec. 21, 2012, Park.
U.S. Appl. No. 13/730,467, Dec. 28, 2012, Park et al.
U.S. Appl. No. 13/730,585, Dec. 28, 2012, Park et al.
U.S. Appl. No. 13/730,608, Dec. 28, 2012, Park et al.
U.S. Appl. No. 13/731,697, filed Dec. 31, 2012, Pavlovskaia et al.
U.S. Appl. No. 13/731,850, filed Dec. 31, 2012, Park.
Final Office Action, U.S. Appl. No. 12/563,809, mailed Mar. 7, 2013, 14 pages.
Non-Final Office Action, U.S. Appl. No. 13/086,275, mailed Feb. 7, 2013, 36 pages.
Non-Final Office Action, U.S. Appl. No. 12/546,545, mailed Mar. 13, 2013, 10 pages.
Notice of Allowance, U.S. Appl. No. 11/924,425, mailed Feb. 5, 2013, 16 pages.
Notice of Allowance, U.S. Appl. No. 29/394,882, mailed Feb. 4, 2013, 32 pages.
Notice of Allowance, U.S. Appl. No. 12/111,924, mailed Mar. 11, 2013, 14 pages.
Notice of Allowance, U.S. Appl. No. 13/573,662, mailed Mar. 19, 2013, 34 pages.
Response to Final Office Action, U.S. Appl. No. 12/546,545, filed Feb. 20, 2013, 13 pages.
Response to Final Office Action, U.S. Appl. No. 12/636,939, filed Apr. 8, 2013, 10 pages.
Response to Non-Final Office Action, U.S. Appl. No. 12/390,667, filed Feb. 26, 2013, 36 pages.
Response to Non-Final Office Action, U.S. Appl. No. 11/641,569, filed Apr. 3, 2013, 9 pages.
Response to Restriction Requirement, U.S. Appl. No. 12/760,388, filed Apr. 5, 2013, 7 pages.
Response to Restriction, U.S. Appl. No. 13/573,662, filed Feb. 8, 2013, 8 pages.
Restriction Requirement, U.S. Appl. No. 12/760,388, mailed Mar. 6, 2013, 7 pages.

* cited by examiner

ARTHROPLASTY DEVICES AND RELATED METHODS

TECHNICAL FIELD

The methods and apparatuses described herein relate generally to the field of implants, as well as jigs that may be used to assist in positioning implants at a target site. More specifically, the methods and apparatuses described herein relate to the field of rapid production of high volumes of arthroplasty jigs and/or arthroplasty implants.

BACKGROUND

Over time and through repeated use, bones and joints can become damaged or worn. For example, repetitive strain on bones and joints (e.g., through athletic activity), traumatic events, and certain diseases (e.g., arthritis) can cause cartilage in joint areas to wear down. As a result, fluid can accumulate in these joint areas, resulting in pain, stiffness, and decreased mobility.

Arthroplasty procedures can be used to repair damaged joints. During a typical arthroplasty procedure, an arthritic or otherwise dysfunctional joint can be remodeled or realigned, or an implant can be implanted into the damaged region. Arthroplasty procedures may take place in any of a number of different regions of the body, such as a knee, a hip, a shoulder, or an elbow.

As mentioned above, during some arthroplasty procedures, an implant may be implanted into the damaged region. The implant may provide support and structure to the damaged region, and may help to restore the damaged region, thereby enhancing its functionality. Prior to implantation of the implant in the damaged region, the damaged region can be prepared to receive the implant. For example, in a knee arthroplasty procedure, one or more of the bones in the knee area, such as the femur and/or the tibia, may be treated (e.g., cut, drilled, reamed, and/or resurfaced) to provide one or more surfaces that can align with the implant and thereby accommodate the implant.

Prior to treating any regions of a bone, it is important to correctly determine the location at which the treatment will take place. In some methods, an arthroplasty jig may be used to accurately position a finishing instrument, such as a cutting, drilling, reaming, or resurfacing instrument. The arthroplasty jig may, for example, include one or more apertures and/or slots that are configured to accept such an instrument. In certain variations, an arthroplasty jig may be customized to correspond to a particular patient's anatomy. For example, while individual human knees share some characteristics, they also can differ from each other in certain ways. As an example, knee alignment (e.g., valgus and varus) can vary from patient to patient. The use of a customized arthroplasty jig may enhance the precision of any cuts or other modifications that are made to a damaged region, such as a damaged knee region, during surgery to repair or restore the damaged region. For at least these reasons, customized arthroplasty jigs can provide for an effective and efficient arthroplasty procedure.

A relatively high number of knee replacement surgeries are conducted each year, and the total number of knee replacement surgeries is expect to continue to grow. For example, it is estimated that approximately 500,000 knee replacement surgeries were performed in the United States in 2005, and it is projected that approximately 1,370,000 knee replacement surgeries will be performed in the United States in 2030. Accordingly, it would be desirable to manufacture a relatively high volume of customized arthroplasty jigs in a relatively short period of time, to be able to meet the demand for quality products. It would also be desirable to economically manufacture a relatively high volume of customized arthroplasty jigs.

BRIEF SUMMARY

Described here are methods and apparatuses that may be used to manufacture a relatively high volume of customized arthroplasty jigs in a relatively short period of time. Certain of the apparatuses described here include an automated mechanical system and at least one rapid production machine, such as a plurality of rapid production machines. Some of the methods described here generally comprise activating the automated mechanical system so that it transports an arthroplasty jig blank to a rapid production machine that is configured to form an arthroplasty jig from the arthroplasty jig blank. After transporting the first arthroplasty jig blank, the automated mechanical system transports another arthroplasty jig blank to another component of the same rapid production machine, or to another rapid production machine. The second component or second rapid production machine also is configured to form an arthroplasty jig from the arthroplasty jig blank. The arthroplasty jigs that are formed by the two different components of the same rapid production machine, or by the two different rapid production machines, have different configurations. Thus, the apparatus and method may be used to produce multiple different customized arthroplasty jigs.

The method can be repeated as desired, so that the automated mechanical system continues to bring arthroplasty jig blanks to the rapid production machine or machines. As the arthroplasty jigs are formed, the automated mechanical system can remove the arthroplasty jigs from the rapid production machines, and transport them to another location, such as a temporary storage site. During operation, the automated mechanical system may be in communication with a computer that provides the automated mechanical system with machining instructions for each arthroplasty jig blank that is transported to a rapid production machine. Each machining instruction can be unique to the particular anatomy of a patient, and thus can result in the production of an arthroplasty jig that is customized to that patient.

Certain variations of the apparatuses may be configured to produce at least 30 customized arthroplasty jigs per hour, at least 50 customized arthroplasty jigs per hour, or at least 100 customized arthroplasty jigs per hour. Some variations of the apparatuses may include at least one rapid production machine that is configured to produce one customized arthroplasty jig every three minutes, five minutes, or ten minutes. The rapid production machines and the apparatuses generally may be able to produce customized arthroplasty jigs at a relatively high rate. Thus, the current high demand and projected future high demand for customized arthroplasty jigs may be satisfied, without resulting in a sacrifice in quality.

The rapid production machines may be, for example, computer numerical control (CNC) machines or stereo-lithograph (SLA) machines, or a combination thereof. In some variations in which the rapid production machines include CNC machines, one or more of the CNC machines may be a four-axis CNC machine or a five-axis CNC machine. Some variations of the apparatuses may include two or more rapid production machines, such as four, five, six, eight, or ten rapid production machines. Furthermore, the rapid production machines may be arranged in any of a number of different ways. For example, the rapid production machines may be arranged to form one or more rows, or may be arranged in a generally circular formation. In certain variations, the rapid production machines may be arranged in such a way as to form one or more spaces through which the automated mechanical system can enter and/or exit.

The automated mechanical system may be configured to remove an arthroplasty jig from a rapid production machine once the formation of the arthroplasty jig has been completed. The automated mechanical system may further be configured to transport the completed arthroplasty jig from the rapid production machine to a station or site. The station or site may, for example, be configured to clean and/or package the arthroplasty jigs, or to store the arthroplasty jigs.

The automated mechanical system may transport the arthroplasty jig blanks and the arthroplasty jigs in any selected order. As an example, the automated mechanical system may transport a first arthroplasty jig blank to a first rapid production machine, and then may transport a second arthroplasty jig blank to a second rapid production machine. Thereafter, the automated mechanical system may remove the completed arthroplasty jig from the first rapid production machine and transport it to a cleaning and packaging station. Alternatively, the automated mechanical system may transport a third arthroplasty jig blank to a third rapid production machine. The order in which the automated mechanical system operates can be selected as desired.

DETAILED DESCRIPTION

Described here are methods and apparatuses for manufacturing a plurality of customized arthroplasty jigs. It should be understood from the outset that while methods of making customized knee arthroplasty jigs are described in detail here, the methods may be used, and are contemplated for use, in making any type of arthroplasty jigs, including, for example, arthroplasty jigs that are suited for use in the hip, shoulder, or elbow.

In general, the methods include using an apparatus comprising an automated mechanical system and at least one rapid production machine that forms the customized arthroplasty jigs. In some variations, the apparatus may include multiple rapid production machines. The automated mechanical system can deliver arthroplasty jig blanks to the rapid production machine or machines, and can communicate machining instructions from a computer to the rapid production machine or machines. Upon receiving machining instructions from the automated mechanical system, a rapid production machine can machine an arthroplasty jig blank to form a customized arthroplasty jig according to the instructions. The automated mechanical system can also remove completed arthroplasty jigs from the rapid production machine or machines, thereby freeing the rapid production machine or machines to form additional arthroplasty jigs. In some variations, the automated mechanical system can transport completed arthroplasty jigs to other stations or sites of the apparatus, such as a finishing station that can clean and/or package the completed arthroplasty jigs. This use of the automated mechanical system and the rapid production machine or machines may result in the relatively efficient and productive manufacture of customized arthroplasty jigs.

Figure 1:
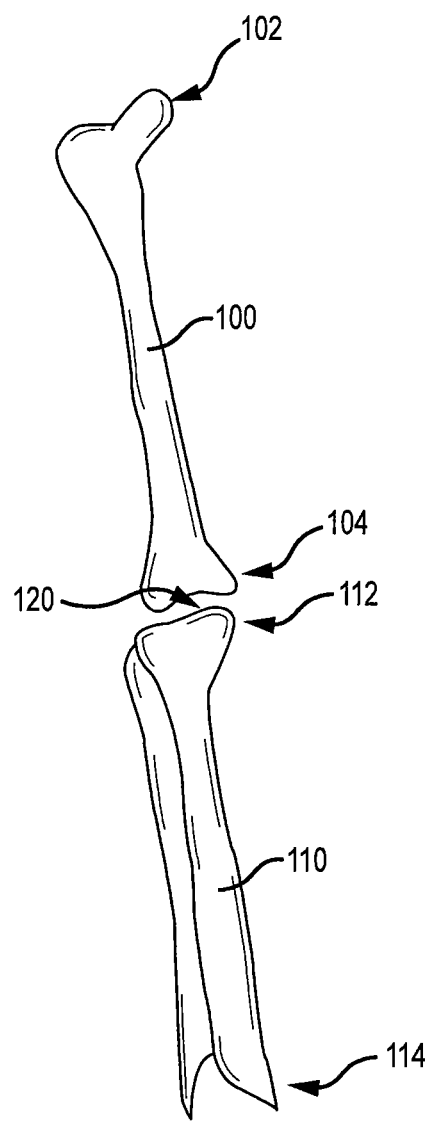
FIG. 1 is an illustration of leg bones of a subject.

Turning now to the figures, FIG. 1 is an illustration of the leg bones of a human subject. As shown in FIG. 1, the leg bones include a femur (100) having an anterior end (102) and a posterior end (104), and a tibia (110) having an anterior end (112) and a posterior end (114). A joint (120) is formed between femur (100) and tibia (110), and may, as a result of damage or wear, require repair or restoration using, for example, an arthroplasty procedure.

As discussed above, in some variations of an arthroplasty procedure, one or more arthroplasty jigs may be employed to help prepare the damaged region for an implant. The arthroplasty jigs may be used, for example, to aid in the correct placement of finishing instruments, such as cutting, drilling, reaming, and resurfacing instruments. As an example, some arthroplasty methods may include using an arthroplasty jig to accurately position a reciprocating saw blade. The reciprocating saw blade may be used, for example, to cut the damaged bone region to provide one or more planar surfaces. The planar surfaces may assist in the alignment and positioning of an implant at a target site in the damaged bone region. Arthroplasty jigs may also be used, for example, to position one or more pins that secure an implant to a target site in the damaged bone region.

Figure 2A:
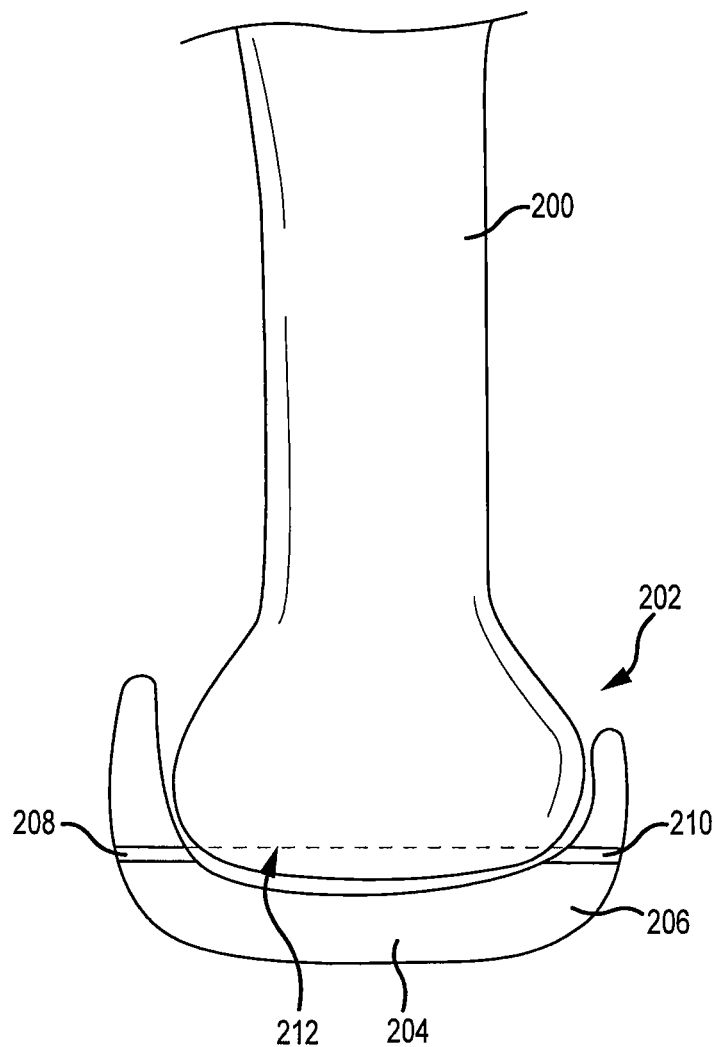
FIG. 2A is an illustration of a portion of a femur of a subject, and an arthroplasty jig engaged with the portion of the femur.
Figure 2B:
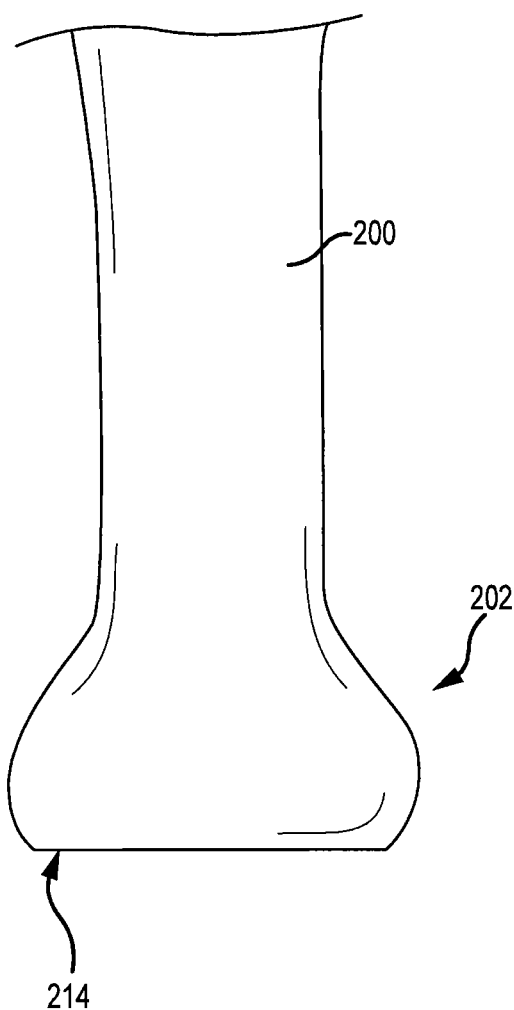
FIG. 2B is an illustration of the portion of the femur of FIG. 2A, after the portion has been cut using a cutting instrument.

An exemplary femoral arthroplasty jig is shown in FIG. 2A. As shown in FIG. 2A, a femur (200) has a posterior end (202). An arthroplasty jig (204) is aligned with posterior end (202), and has a body (206) including two slots (208) and (210). Slots (208) and (210) can be used, for example, to position a cutting instrument (e.g., a reciprocating saw blade). The cutting instrument, in turn, can be used to form a cut (212) that removes a portion of posterior end (202) of femur (200). The result, as shown in FIG. 2B, is a planar surface (214) along posterior end (202) of femur (200). Planar surface (214) may, for example, align with a corresponding planar surface of an implant that is implanted into a damaged region of the knee that is at least partially defined by femur (200).

Figure 3A:
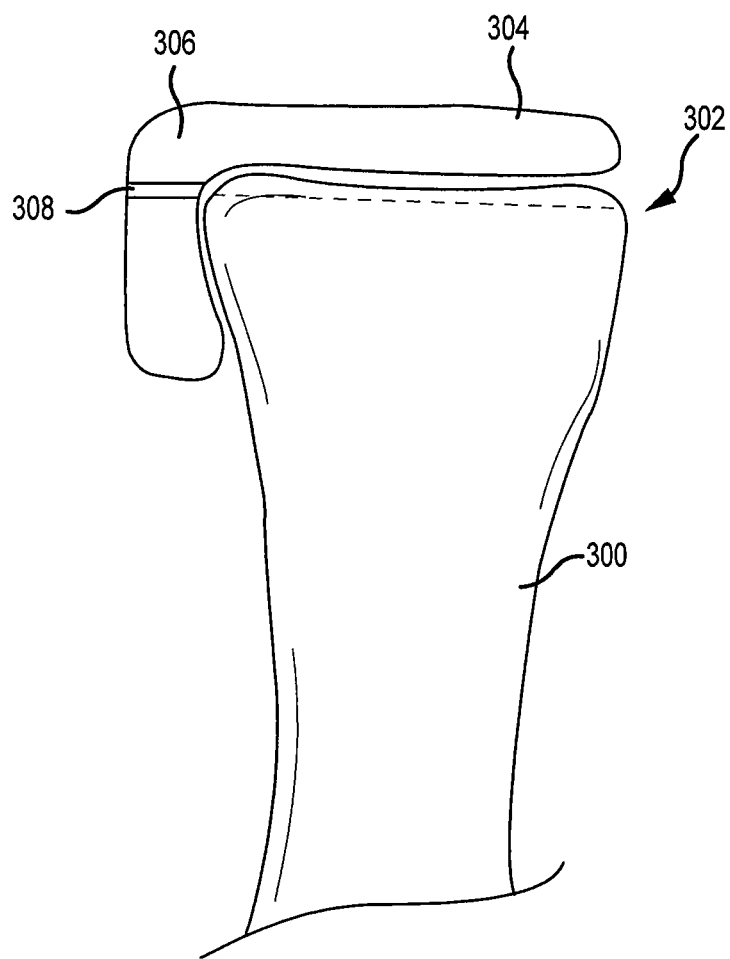
FIG. 3A is an illustration of a portion of a tibia of a subject, and an arthroplasty jig engaged with the portion of the tibia.
Figure 3B:
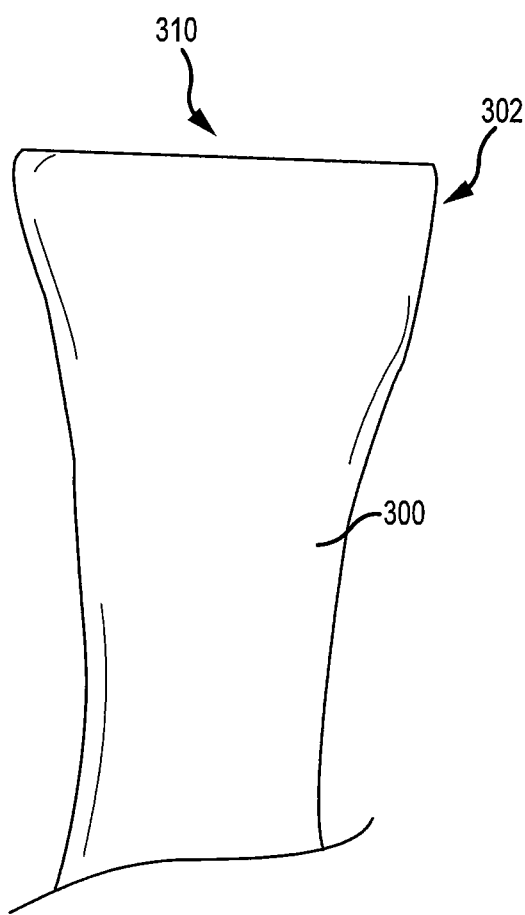
FIG. 3B is an illustration of the portion of the tibia of FIG. 3A, after the portion has been cut using a cutting instrument.

Similarly, an exemplary tibial arthroplasty jig is shown in FIG. 3A. As shown in FIG. 3A, a tibia (300) has an anterior end (302). An arthroplasty jig (304) is aligned with anterior end (302), and has a body (306) including a slot (308). Slot (308) can be used for placement of a cutting instrument (e.g., a reciprocating saw blade). The cutting instrument can be used, for example, to form a cut that removes a portion of anterior end (302) of tibia (300). The result, as shown in FIG. 3B, is a planar surface (310) along anterior end (302) of tibia (300). Planar surface (310) may, for example, align with a corresponding planar surface of an implant that is implanted into a damaged region of the knee that is at least partially defined by tibia (300).

As discussed above, arthroplasty jigs may be customized so that the accuracy of their positioning (and, therefore, the accuracy with which they position finishing instruments) can be enhanced. Various methods may be used to form customized arthroplasty jigs, such as the methods described, for example, in U.S. patent application Ser. No. 10/146,862, filed on May 15, 2002, which is hereby incorporated by reference in its entirety.

Figure 4:
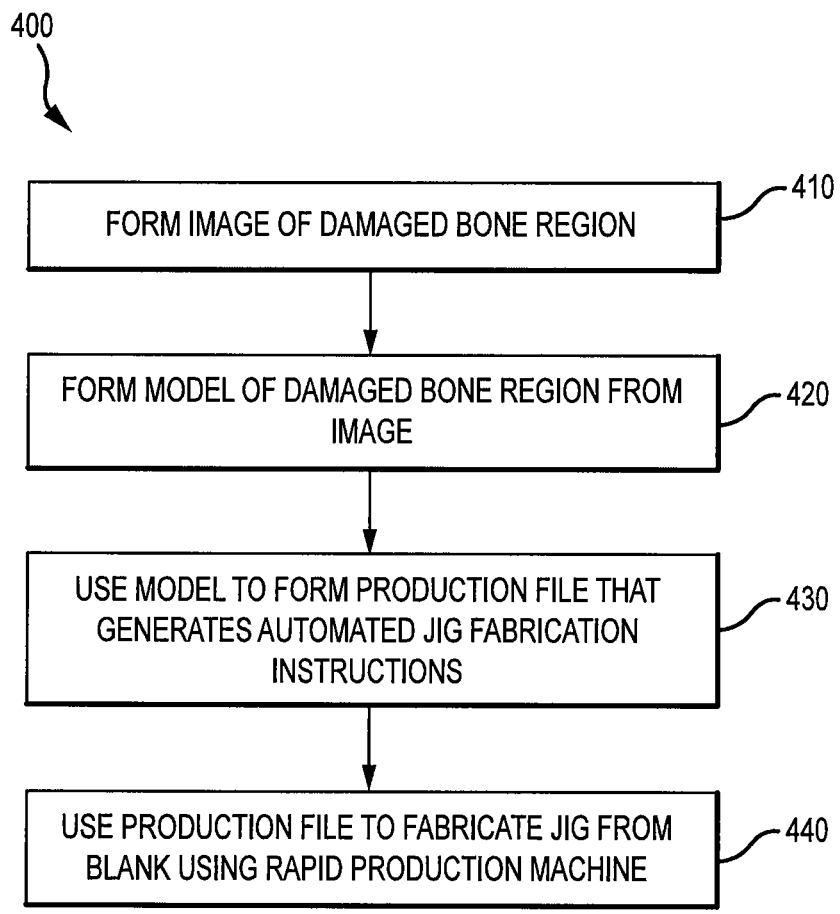
FIG. 4 is a flowchart representation of a method of treating a damaged bone region of a subject.

One variation of a method (400) that may be used to form customized arthroplasty jigs is depicted as a flowchart in FIG. 4. As shown in FIG. 4, this illustrative method comprises forming an image of a damaged bone region of a patient (410) using, for example, computer tomography (CT) and/or magnetic resonance imaging (MRI). The image may be formed specifically of the damaged bone region, or may include portions of the bone that are not damaged. As an example, an image of a damaged knee region may include the entirety of the knee region, as well as the entirety of the associated femur and tibia. After the image has been formed, a three-dimensional model of the damaged bone region is formed from the image (420). The model may be formed, for example, by using the image to determine location coordinate values of each of a sequence of spaced apart surface points in the damaged bone region, and then using a mathematical model to estimate or compute the three-dimensional model. Thereafter, the model and the image are used to generate a production file that provides automated arthroplasty jig fabrication instructions (430) to a rapid production machine, which fabricates a customized arthroplasty jig from an arthroplasty jig blank according to the instructions (440).

Customized arthroplasty jigs may provide many advantages. A hospital that uses customized arthroplasty jigs may be able to maintain a relatively low inventory of the arthroplasty jigs, because the arthroplasty jigs can be provided to the hospital on an as-needed basis, and are customized to particular patients. Accordingly, the hospital may not need to maintain multiple arthroplasty jigs of different sizes and shapes in inventory. Similarly, the use of customized arthroplasty jigs may lead to a decrease in the total number of operating tools required to be in the operating room. Furthermore, customized arthroplasty jigs may provide for enhanced implant alignment and positioning relative to non-customized arthroplasty jigs. This enhanced alignment and positioning may, in turn, decrease the likelihood of follow-up surgery (e.g., to adjust the alignment of the implant), and increase the useful life of the implant. Moreover, patients may experience reduced recovery time when customized arthroplasty jigs are used, in comparison to non-customized arthroplasty jigs. Customized arthroplasty jigs may result in fewer complications during surgery than non-customized arthroplasty jigs, and may allow a damaged bone region to be restored to an earlier, better condition.

Figure 5:
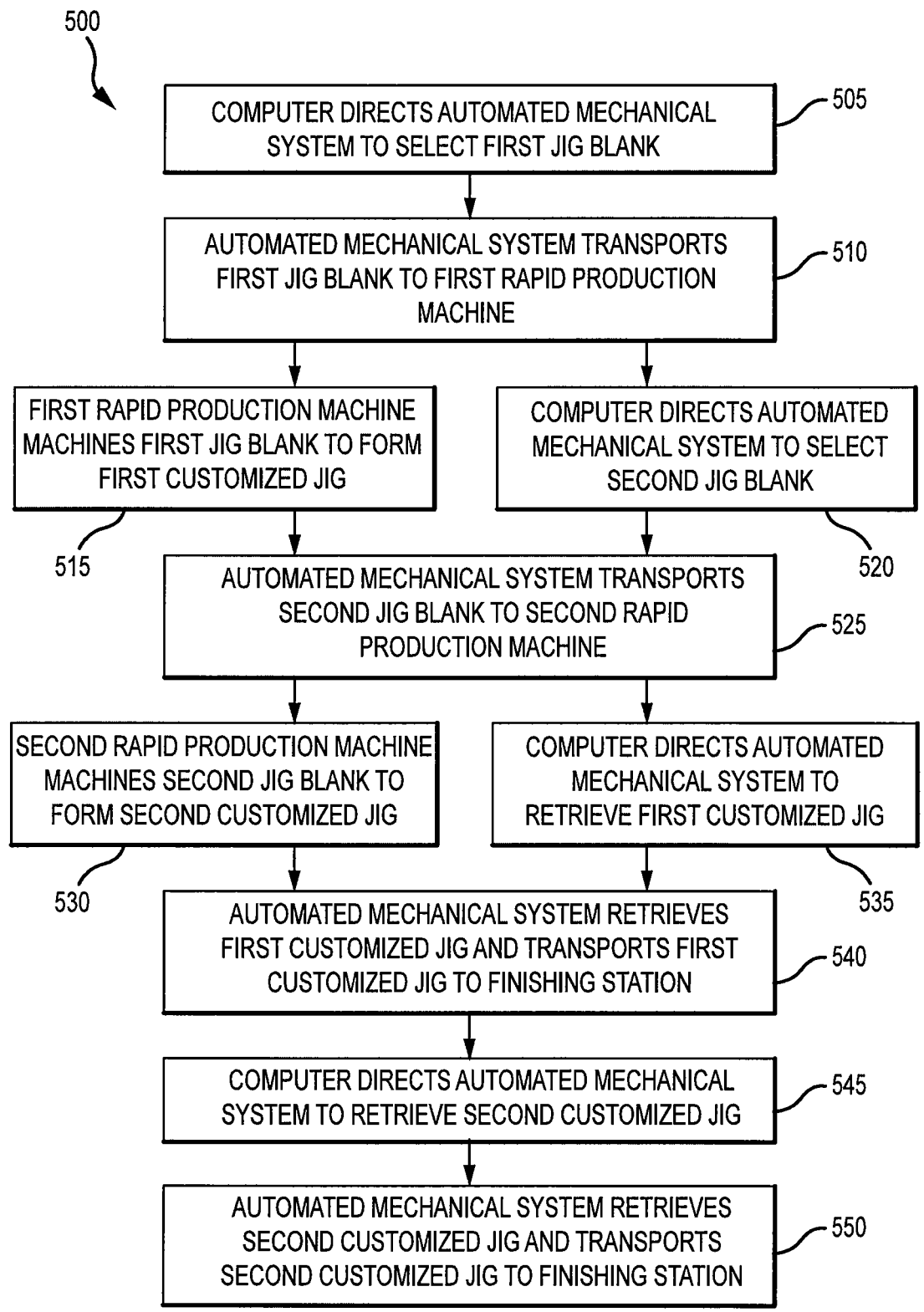
FIG. 5 is a flowchart representation of a method of manufacturing arthroplasty jigs.

At least for the reasons discussed above, it would be desirable to be able to manufacture a relatively high volume of customized arthroplasty jigs in a relatively short period of time. FIG. 5 provides a flowchart representation of one variation of a method (500) that may be used to produce high volumes of customized arthroplasty jigs efficiently.

As shown in FIG. 5, a computer that is in communication with an automated mechanical system directs the automated mechanical system to select a first arthroplasty jig blank (505). After selecting the first arthroplasty jig blank, the automated mechanical system transports the first arthroplasty jig blank to a first rapid production machine (510). The automated mechanical system also communicates customized machining instructions from the computer to the first rapid production machine, so that the first rapid production machine can machine the first arthroplasty jig blank to form a first customized arthroplasty jig (515). The computer then directs the automated mechanical system to select a second arthroplasty jig blank (520), which the automated mechanical system transports to a second rapid production machine (525). The automated mechanical system also communicates customized machining instructions from the computer to the second rapid production machine, so that the second rapid production machine can machine the second arthroplasty jig blank to form a second customized arthroplasty jig (530). The computer then directs the automated mechanical system to retrieve the completed first customized arthroplasty jig (535). Accordingly, the automated mechanical system retrieves the first customized arthroplasty jig and transports the first customized arthroplasty jig to a finishing station (540). Finally, the computer directs the automated mechanical system to retrieve the second customized arthroplasty jig (545). After retrieving the second customized arthroplasty jig, the automated mechanical system transports the second customized arthroplasty jig to the finishing station (550).

The steps in the above-described method (500) can be repeated as desired, to produce any number of customized arthroplasty jigs, such as 100, 500, or 1000 customized arthroplasty jigs. Furthermore, the steps need not be performed in the specific order described with reference to FIG. 5. For example, an automated mechanical system may pick up eight arthroplasty jig blanks and deliver them to eight individual rapid production machines, prior to retrieving any completed customized arthroplasty jigs from the rapid production machines. Additionally, in some variations of the method, an automated mechanical system may transport multiple arthroplasty jig blanks to a single rapid production machine, or may pick up multiple arthroplasty jig blanks at once, and then distribute the arthroplasty jig blanks to individual rapid production machines. Moreover, in certain variations of the method, one or more steps may be omitted. For example, the automated mechanical system may not transport the customized arthroplasty jigs to a finishing station.

In certain variations of the above-described method, an apparatus may be used to manufacture, for example, at least 30 customized arthroplasty jigs per hour, at least 50 customized arthroplasty jigs per hour, or at least 100 customized arthroplasty jigs per hour. Some variations of the apparatuses may include at least one rapid production machine that is configured to produce one customized arthroplasty jig every three minutes, five minutes, or ten minutes. These are just specific examples and are not intended to be limiting; an apparatus may be used to manufacture a lower or higher number of customized arthroplasty jigs per hour, and/or a rapid production machine may be configured to produce an arthroplasty jig in a shorter or longer period of time.

The arthroplasty jigs described herein may be individually packaged, or may be packaged together with other arthroplasty jigs (e.g., for shipment to a single customer). In some variations, the method may include packaging a customized arthroplasty jig in a kit with other components or devices that are used during an arthroplasty procedure.

While the above-described method involves the manufacture of customized arthroplasty jigs having different configurations, in certain variations, a method may include manufacturing two or more arthroplasty jigs having the same configuration. As an example, multiple copies of an arthroplasty jig that has been customized for a particular patient may be manufactured. As another example, in some variations, the above-described apparatus may be used to manufacture one or more non-customized arthroplasty jigs. Advantageously, the apparatus may manufacture these arthroplasty jigs at a relatively high rate. Thus, relatively high volumes of non-customized arthroplasty jigs may be produced in a relatively short period of time.

Figure 6:
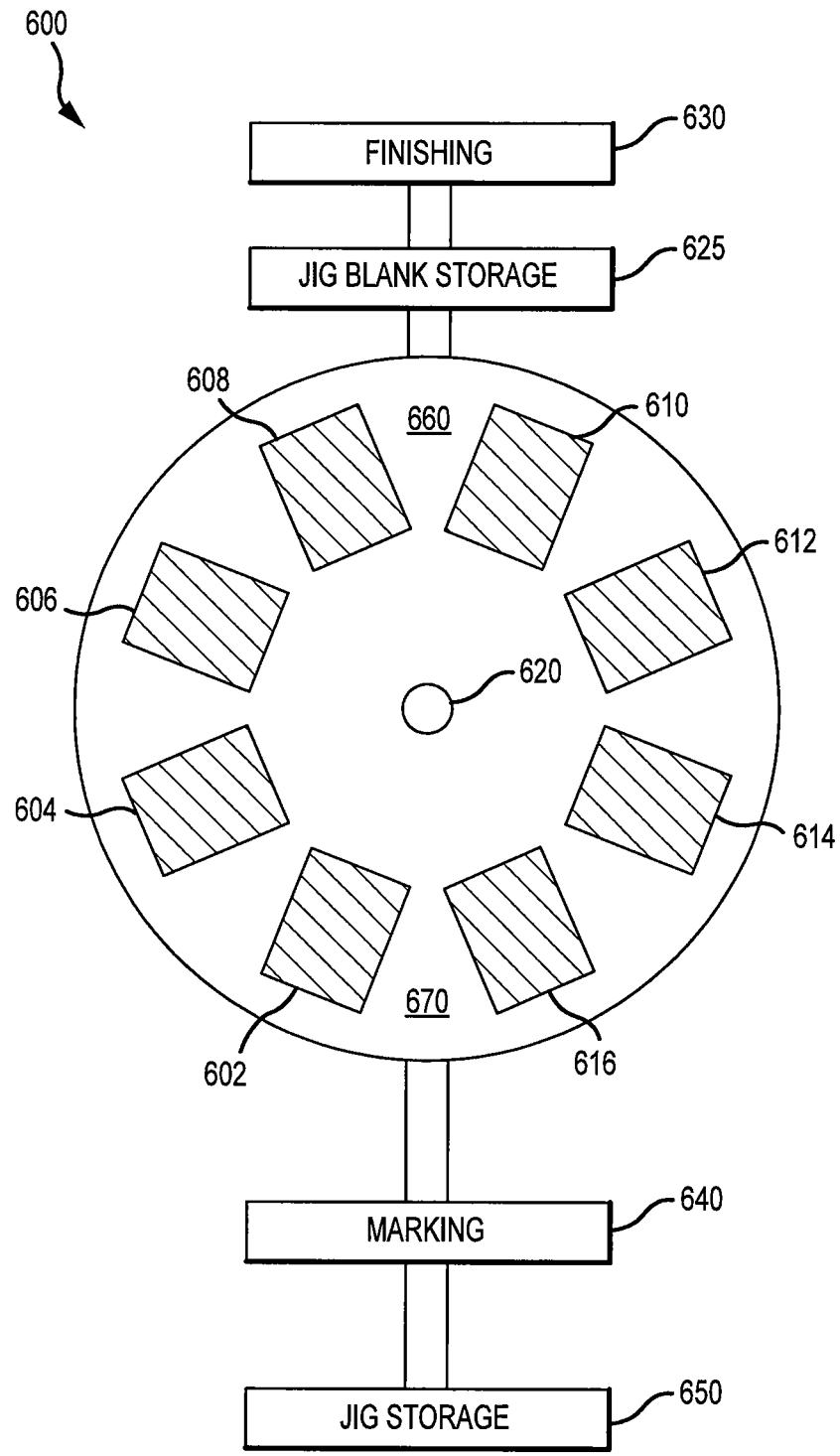
FIG. 6 is an illustration of an apparatus for manufacturing arthroplasty jigs.

FIG. 6 provides a depiction of an apparatus that may be used to perform the method described with reference to FIG. 5. As shown in FIG. 6, an apparatus (600) includes eight rapid production machines (602, 604, 606, 608, 610, 612, 614, and 616) arranged in a generally circular formation, as well as an automated mechanical system (as shown, a robot (620)) that is capable of moving between the different rapid production machines. Apparatus (600) further includes an arthroplasty jig blank storage site (625), a finishing station (630), a marking station (640), and an arthroplasty jig storage site (650).

When apparatus (600) is activated, robot (620) selects an arthroplasty jig blank from arthroplasty jig blank storage site (625). Robot (620) then transports the arthroplasty jig blank to one of the rapid production machines, such as rapid production machine (608). Robot (620), which is in communication with a computer, transmits customized machining instructions from the computer to the rapid production machine so that the rapid production machine will produce a customized arthroplasty jig. The rapid production machine then machines the arthroplasty jig blank to form the customized arthroplasty jig, while robot (620) returns to arthroplasty jig blank storage site (625) to select another arthroplasty jig blank. Robot (620) then transports the other arthroplasty jig blank to another rapid production machine, such as rapid production machine (610), and transmits customized machining instructions from the computer to the rapid production machine. The customized machining instructions that are provided to the first rapid production machine will generally be different from the customized machining instructions that are provided to the second rapid production machine, as the two sets of instructions typically will correspond to different patients' anatomies.

After an arthroplasty jig has been produced, robot (620) retrieves the arthroplasty jig from the rapid production machine that produced it, and transports the arthroplasty jig to finishing station (630). At finishing station (630), the arthroplasty jig can, for example, be cleaned and/or packaged. As an example, the arthroplasty jig may be sterilized and packaged in a protective packaging. Examples of sterilization methods that may be used at the finishing station include chemical sterilization, e-beam sterilization, and gamma ray sterilization. In some variations, an arthroplasty jig may be sterilized by autoclaving. In certain variations, an arthroplasty jig may be sterilized at a different location, either as an alternative to or in addition to being sterilized at the finishing station. For example, an arthroplasty jig may be sterilized at a hospital (e.g., by autoclaving).

Once the arthroplasty jig has completed its time at the finishing station, robot (620) can retrieve the arthroplasty jig and transport it, for example, to marking station (640). At the marking station, the arthroplasty jig and/or any packaging around the arthroplasty jig may be marked or labeled. Examples of information that may be included on the marks or labels include inventory control numbers, manufacture dates, patient data, physician or hospital data, company logos, barcodes, etc. The marking or labeling may be conducted using, for example, laser technology or machine engraving, or simply adhesive stickers that are, for example, applied directly to the arthroplasty jig packaging. After the arthroplasty jig has been marked and/or labeled, robot (620) transports the arthroplasty jig to arthroplasty jig storage site (650), where the arthroplasty jig remains until it is moved elsewhere (e.g., until it is shipped to a customer).

In some variations, the rapid production machines are computer numerical control machines. Other examples of rapid production machines that may be used include stereo-lithograph machines. While apparatus (600) is shown as having eight rapid production machines, an apparatus can have a lower (e.g., two, four, or six) or higher (e.g., ten, twelve, or fourteen) number of rapid production machines. An apparatus may have an even number of rapid production machines, or an odd number of rapid production machines. The rapid production machines may all be of the same type, or may be different from each other. In certain variations, an apparatus may include a rapid production machine having at least two different components that each are configured to form an arthroplasty jig from an arthroplasty jig blank. Thus, the rapid production machine may be used to produce multiple arthroplasty jigs. In some variations, an apparatus may include just one rapid production machine.

Figure 7:
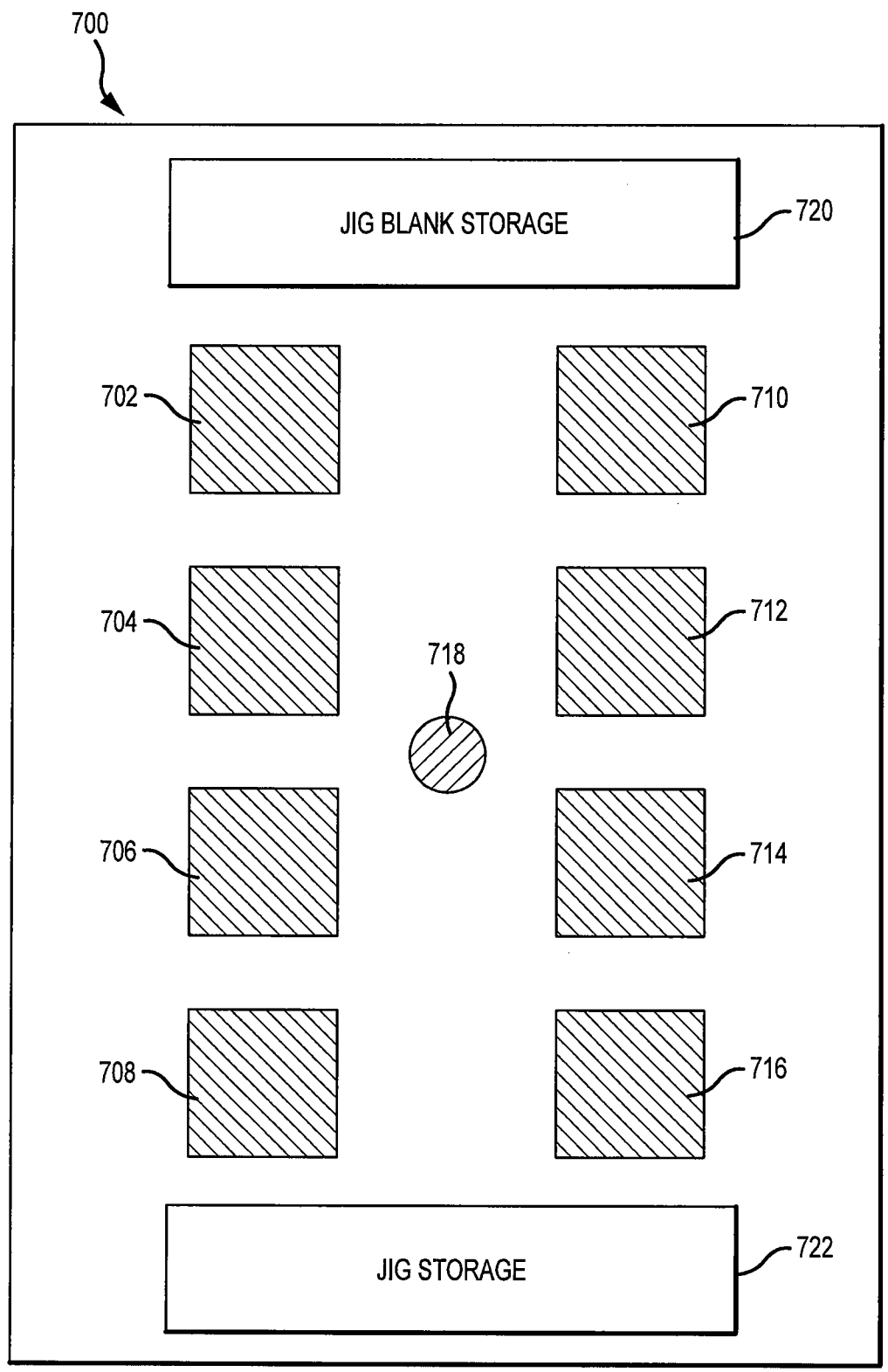
FIG. 7 is an illustration of an apparatus for manufacturing arthroplasty jigs.

While the rapid production machines in apparatus (600) are arranged in a generally circular formation, other formations may be used. As an example, rapid production machines may be arranged in one or more rows, such as two rows, three rows, four rows, five rows, or ten rows. For example, FIG. 7 shows an apparatus (700) including eight rapid production machines (702, 704, 706, 708, 710, 712, 714, and 716) that are arranged in two rows of four rapid production machines each. Apparatus (700) further includes an automated mechanical system (as shown, a robot (718)), an arthroplasty jig blank storage site (720), and an arthroplasty jig storage site (722). The arrangement of the rapid production machines in apparatus (700) may, for example, allow robot (718) to move relatively easily between the arthroplasty jig blank storage site, the various rapid production machines, and the arthroplasty jig storage site.

As further examples, rapid production machines may be arranged in square or oval formations, or may be arranged in other regular formations (such as an X), or in irregular formations. The formation in which the rapid production machines are arranged may be selected, for example, based on the projected path of movement of the automated mechanical system through the apparatus. For example, and referring back to FIG. 6, the rapid production machines of apparatus (600) are arranged to provide a pathway (660) for robot (620) to easily access arthroplasty jig blank storage site (625) and finishing station (630), as well as a pathway (670) for robot (620) to easily access marking station (640) and arthroplasty jig storage site (650). In some variations, the formation in which the rapid production machines are arranged may be selected based on the size and/or configuration of the available manufacturing space.

While the above-described apparatuses include one arthroplasty jig blank storage site and one arthroplasty jig storage site, an apparatus may include multiple storage sites for arthroplasty jig blanks and/or arthroplasty jigs. Similarly, an apparatus may include multiple finishing stations and/or marking stations, or may not include some or all of these sites or stations. The components of an apparatus may be selected according to the particular needs and requirements of the manufacturing process being conducted.

As discussed above, in some variations, an automated mechanical system may be a robot. While a robot that is in communication with one computer has been described, in some variations, a robot or another type of automated mechanical system may be in communication with more than one computer, such as two computers, five computers, or ten computers. In certain variations in which the automated mechanical system is a robot, the robot may be stationary or may, for example, be configured to move along one or more tracks and/or rails. In some variations, the robot may be in the form of an arm with a gripper at its end. The arm may be formed of, for example, two metal bars that are connected together by a movable joint. The gripper may be used to grasp and temporarily hold onto an arthroplasty jig or an arthroplasty jig blank. In certain variations, the gripper may have five or six degrees of freedom. While a gripper has been described, a robot that is appropriate for use in the above-described apparatuses may alternatively or additionally include one or more other features that allow the robot to temporarily hold onto an arthroplasty jig or an arthroplasty jig blank. As an example, a robot may include a component that temporarily holds onto an arthroplasty jig or an arthroplasty jig blank via suction. Examples of robots that are commercially available and that may be used in the above-described apparatuses include robots manufactured by FANUC Robotics (Rochester Hills, Mich.).

In some variations, an apparatus may include multiple automated mechanical systems, such as two, five, or ten automated mechanical systems. The automated mechanical systems may all be the same type of automated mechanical system, or may be different from each other. Furthermore, the automated mechanical systems may all communicate with the same computer, or may communicate with different computers. While robots have been described as examples of automated mechanical systems, other types of automated mechanical systems, such as conveyor belts, may be used in the apparatuses and methods described herein.

The arthroplasty jig blanks and arthroplasty jigs described herein may be formed of any of a number of different materials. They may be formed of just one material, or multiple materials, such as a blend of different materials or layers of different materials. Examples of suitable materials include polymers, metals, ceramics, metal alloys, and combinations thereof. Specific examples of polymers include acetal resins (e.g., Delrin®), polyetheretherketones (PEEK), polycarbonates, polyamides, polyesters, polystyrenes, polyacrylates, vinyl polymers, and polyurethanes. Specific examples of metals and metal alloys include gold, platinum, palladium, stainless steel, cobalt alloys (e.g., Elgiloy®), and nickel-titanium alloys (e.g., Nitinol™). In some variations, the arthroplasty jig blanks may be formed of one or more plastics. In such variations, the arthroplasty jig blanks may be formed, for example, using injection molding technology and/or thermal plastic press forming technology. In certain variations, an arthroplasty jig may be intended to be disposable, while in other variations, an arthroplasty jig may be intended to be reusable. The materials out of which an arthroplasty jig is formed may be selected with these and/or other criteria in mind.

In some variations, an arthroplasty jig may include one or more materials that were not included in the arthroplasty jig blank from which the arthroplasty jig was formed. This may occur, for example, as a result of the arthroplasty jig being processed through the finishing station, where the arthroplasty jig may be coated with a coating material, such as an antibacterial coating material.

The arthroplasty jig blanks that are used in an apparatus may have any of a number of different configurations, sizes, and/or shapes. As an example, some arthroplasty jig blanks may be in the form of blocks of material. As another example, some arthroplasty jig blanks may be designed for use with the left side of a patient's body (e.g., a left knee), while other arthroplasty jig blanks are designed for use with the right side of a patient's body (e.g., the right knee). The arthroplasty jig blanks may have certain of these types of features, or may be relatively feature-less. In certain variations of the methods described here, a computer may provide instructions to an automated mechanical system regarding the configuration, size, and/or shape of arthroplasty jig blank to select to form a particular customized arthroplasty jig.

While arthroplasty jigs having one or two slots have been shown, arthroplasty jigs can have any number of slots, apertures, grooves, and/or ridges. Furthermore, arthroplasty jigs can be configured for use in forming more than one planar surface in a damaged bone region. For example, an arthroplasty jig may be used to form two or three planar surfaces in a damaged bone region. The multiple planar surfaces may correspond to multiple planar surfaces in an implant that is to be inserted into the damaged bone region. Moreover, the slots, apertures, grooves, and/or ridges may be used for other purposes besides the aforementioned cutting, drilling, reaming, and resurfacing. For example, apertures in an arthroplasty jig may be used to help position one or more pins that can, for example, be used to secure an implant to a target location.

While methods and apparatuses described herein have been described with respect to the manufacture of arthroplasty jigs, some variations of methods and apparatuses may be used to manufacture implants, such as arthroplasty implants. The implants may, for example, be customized to correspond to particular patients' anatomies. Moreover, while arthroplasty procedures have been described, the jigs and implants described herein may be used in any of a number of different procedures, including, for example, spinal surgery.

In some variations, a manufacturing process may include the use of multiple apparatuses, such as five or ten apparatuses. The apparatuses may operate in conjunction to produce a relatively high output of jigs and/or implants over a relatively short period of time. In certain variations, one apparatus may be configured to manufacture one type of jig or implant, while another apparatus may be configured to manufacture another type of jig or implant. As an example, one apparatus may be configured to manufacture arthroplasty jigs for one customer, while another apparatus is configured to manufacture arthroplasty jigs for a different customer. As another example, one apparatus may be configured to manufacture arthroplasty jigs for left knees, while another apparatus is configured to manufacture arthroplasty jigs for right knees. As an additional example, one apparatus may be configured to manufacture arthroplasty jigs, while another apparatus is configured to manufacture arthroplasty implants.

Furthermore, while one method of manufacturing a customized arthroplasty jig has been described above, other methods may be used. For example, one-, two-, and three-dimensional measurements of a target site may be taken using lasers, electromagnetic or optical tracking systems, or other imaging methods. As an example, while CT and MRI have been described, other imaging methods that may be used include X-ray technology, optical coherence tomography, ultrasound imaging, and optical imaging. In some variations, multiple imaging techniques may be used together to image a target site. Moreover, the measurements that are used to image an area may be taken in a non-invasive manner, or may be taken intra-operatively (e.g., using optical, mechanical, and/or ultrasound probes).

While the methods, devices, and apparatuses have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the pending claims.

What is claimed is:

1. A method of manufacturing a plurality of customized arthroplasty jigs, the method comprising:

activating an automated mechanical system in an apparatus comprising the automated mechanical system, an arthroplasty jig blank storage site comprising a plurality of arthroplasty jig blanks and a plurality of rapid production machines, so that the automated mechanical system physically transports a first arthroplasty jig blank from the arthroplasty jig blank storage site to a first rapid production machine that is configured to machine a first arthroplasty jig from the first arthroplasty jig blank, and so that the automated mechanical system physically transports a second arthroplasty jig blank from the arthroplasty jig blank storage site to a second rapid production machine that is configured to machine a second arthroplasty jig from the second arthroplasty jig blank, wherein the first and second arthroplasty jigs have different configurations, and wherein the automated mechanical system is a robot.

2. The method of claim 1, wherein the automated mechanical system physically transports the first arthroplasty jig blank to the first rapid production machine prior to physically transporting the second arthroplasty jig blank to the second rapid production machine.

3. The method of claim 1, wherein the first and second rapid production machines comprise computer numerical control machines.

4. The method of claim 1, wherein the apparatus comprises eight rapid production machines.

5. The method of claim 1, wherein the automated mechanical system is in communication with a computer.

6. The method of claim 5, wherein the computer provides the automated mechanical system with first machining instructions for machining the first arthroplasty jig.

7. The method of claim 6, wherein the computer provides the automated mechanical system with second machining instructions for machining the second arthroplasty jig.

8. The method of claim 7, wherein the automated mechanical system communicates the first machining instructions to the first rapid production machine so that the first rapid production machine can machine the first arthroplasty jig.

9. The method of claim 8, wherein the automated mechanical system communicates the second machining instructions to the second rapid production machine so that the second rapid production machine can machine the second arthroplasty jig.

10. The method of claim 1, wherein the method comprises producing at least 30 customized arthroplasty jigs per hour.

11. The method of claim 1, wherein the rapid production machines are arranged in rows.

12. The method of claim 1, wherein the rapid production machines are arranged in a circle.

13. The method of claim 1, wherein the automated mechanical system removes the first arthroplasty jig from the first rapid production machine when machining of the first arthroplasty jig has been completed.

14. The method of claim 13, wherein the automated mechanical system transports the first arthroplasty jig from the first rapid production machine to a station that is configured to clean arthroplasty jigs.

15. The method of claim 14, wherein the station also is configured to package the arthroplasty jigs after they have been cleaned.

16. The method of claim 13, wherein the automated mechanical system transports the second arthroplasty jig from the second rapid production machine when machining of the second arthroplasty jig has been completed.

17. A method of manufacturing a plurality of customized arthroplasty jigs, the method comprising:

activating an automated mechanical system in an apparatus comprising the automated mechanical system, an arthroplasty jig blank storage site comprising a plurality of arthroplasty jig blanks and a rapid production machine, so that the automated mechanical system physically transports a first arthroplasty jig blank from the arthroplasty jig blank storage site to a first component of the rapid production machine that is configured to machine a first arthroplasty jig from the first arthroplasty jig blank, and so that the automated mechanical system physically transports a second arthroplasty jig blank from the arthroplasty jig blank storage site to a second component of the rapid production machine that is configured to machine a second arthroplasty jig from the second arthroplasty jig blank, wherein the first and second arthroplasty jigs have different configurations, and wherein the automated mechanical system is a robot in communication with a computer, the computer providing the automated mechanical system with first machining instructions for machining the first arthroplasty jig.

18. The method of claim 17, wherein the rapid production machine comprises a computer numerical control machine.

19. The method of claim 17, wherein the computer provides the automated mechanical system with second machining instructions for machining the second arthroplasty jig.

20. The method of claim 19, wherein the automated mechanical system communicates the first machining instructions to the first component of the rapid production machine so that the first component can machine the first arthroplasty jig.

21. The method of claim 20, wherein the automated mechanical system communicates the second machining instructions to the second rapid production machine so that the second rapid production machine can machine the second arthroplasty jig.

22. The method of claim 17, wherein the method comprises producing at least 30 customized arthroplasty jigs per hour.

* * * * *